(12) United States Patent
Chandraratna

(10) Patent No.: US 6,624,188 B1
(45) Date of Patent: Sep. 23, 2003

(54) METHOD OF TREATMENT WITH COMPOUNDS HAVING RETINOID-LIKE ACTIVITY AND REDUCED SKIN TOXICITY AND LACKING TERATOGENIC EFFECTS

(75) Inventor: Roshantha A. S. Chandraratna, El Toro, CA (US)

(73) Assignee: Allergan, Inc., irvine, CA (US)

( * ) Notice: Subject to any disclaimer, the term of this patent is extended or adjusted under 35 U.S.C. 154(b) by 0 days.

(21) Appl. No.: 08/216,990

(22) Filed: Mar. 23, 1994

Related U.S. Application Data

(62) Division of application No. 07/898,764, filed on Jun. 11, 1992, now Pat. No. 5,324,840.

(51) Int. Cl.$^7$ ..................... A61K 31/382; A61K 31/355

(52) U.S. Cl. ................. 514/432; 514/444; 514/456

(58) Field of Search .......... 549/23, 398, 407; 514/432, 456, 444

(56) References Cited

U.S. PATENT DOCUMENTS

| | | | | |
|---|---|---|---|---|
| 4,096,341 | A | 6/1978 | Frazer | 560/85 |
| 4,326,055 | A | 4/1982 | Loeliger | 542/429 |
| 4,391,731 | A | 7/1983 | Boller et al. | 252/299.62 |

(List continued on next page.)

FOREIGN PATENT DOCUMENTS

| | | |
|---|---|---|
| DE | 3316932 | 11/1983 |
| DE | 3524199 | 1/1986 |
| DE | 3531722 | 3/1986 |
| DE | 3602473 | 7/1987 |
| DE | 3708060 | 9/1987 |

(List continued on next page.)

OTHER PUBLICATIONS

Strickland et al., Cancer Research 43, 5268–5272, Nov. 1983.*

Zouboulis et al., J. Invest. Derm. 96(5) May 1991, 792–796.*

Breitman et al., Proc. Natl. Acad. Sci. 77(5) pp. 2936–2940, May 1980.*

(List continued on next page.)

Primary Examiner—Phyllis G. Spivack
(74) Attorney, Agent, or Firm—Brent A. Johnson; Robert J. Baran; Martin A. Voet

(57) ABSTRACT

A process and pharmaceutical compositions for treating several diseases and conditions which are normally treatable with retinoid like compounds are disclosed where the compound used for the treatment are substantially non-teratogenic and not irritant to the skin. The process is useful for treating female mammals, including humans, who are pregnant or in the child bearing age. An important partial structural feature of the compounds which provides the non-teratogenic effect and lack of irritation of skin is shown by the formula where the partially drawn ring signifies an aromatic ring which may be carbocyclic or heteroaromatic, 6-membered or 5-membered, and may be condensed with another ring. $R_1$ is lower alkyl, Cl, Br, or I, $R_2$ is H, lower alkyl, Cl, Br, or I, and $R_3$ is lower alkyl, Cl, Br, I, or is an ether, thioether, ester, thioester, amine or substituted amine group.

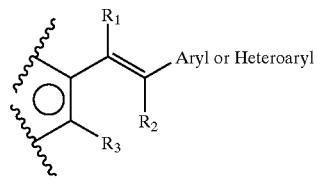

4 Claims, 9 Drawing Sheets

U.S. PATENT DOCUMENTS

| | | | |
|---|---|---|---|
| 4,695,649 A | 9/1987 | Magami et al. | 560/86 |
| 4,723,028 A | 2/1988 | Shudo | 560/8 |
| 4,739,098 A | 4/1988 | Chandraratna | 560/8 |
| 4,740,519 A | 4/1988 | Shroot et al. | 514/443 |
| 4,810,804 A | 3/1989 | Chandraratna | 514/311 |
| 4,826,969 A | 5/1989 | Maignan et al. | 536/55.2 |
| 4,826,984 A | 5/1989 | Berlin et al. | 546/134 |
| 4,833,254 A * | 5/1989 | Berlin et al. | 548/454 |
| 4,855,320 A | 8/1989 | Chatterjee et al. | 514/473 |
| 4,895,868 A | 1/1990 | Chandraratna | 514/432 |
| 4,927,947 A | 5/1990 | Chandraratna | 549/484 |
| 4,980,369 A | 12/1990 | Chandraratna | 514/432 |
| 4,992,468 A | 2/1991 | Chandraratna | 514/532 |
| 5,006,550 A | 4/1991 | Chandraratna | 514/456 |
| 5,013,744 A | 5/1991 | Chandraratna | 514/345 |
| 5,015,658 A | 5/1991 | Chandraratna | 514/432 |
| 5,023,341 A | 6/1991 | Chandraratna | 549/23 |
| 5,037,825 A | 8/1991 | Klaus et al. | 514/233.8 |
| 5,045,551 A | 9/1991 | Chandraratna | 514/337 |
| 5,053,253 A | 10/1991 | Chandraratna | 549/398 |
| 5,068,523 A | 11/1991 | Chandraratna | 514/543 |
| 5,089,509 A | 2/1992 | Chandraratna | 514/337 |
| 5,130,335 A | 7/1992 | Chandraratna | 514/510 |
| 5,134,159 A | 7/1992 | Chandraratna | 514/456 |
| 5,162,546 A | 11/1992 | Chandraratna | 549/23 |
| 5,175,185 A | 12/1992 | Chandraratna | 514/445 |
| 5,183,827 A | 2/1993 | Chandraratna | 514/444 |
| 5,202,471 A | 4/1993 | Chandraratna | 562/473 |
| 5,231,113 A | 7/1993 | Chandraratna | 514/510 |
| 5,234,926 A | 8/1993 | Chandraratna | 514/253 |
| 5,248,777 A | 9/1993 | Chandraratna | 546/165 |
| 5,264,456 A | 11/1993 | Chandraratna | 514/461 |
| 5,264,578 A | 11/1993 | Chandraratna | 546/269 |
| 5,272,156 A | 12/1993 | Chandraratna | 514/314 |
| 5,278,318 A | 1/1994 | Chandraratna | 549/23 |

FOREIGN PATENT DOCUMENTS

| | | |
|---|---|---|
| EP | 0098591 | 1/1984 |
| EP | 0130795 | 1/1985 |
| EP | 0176032 | 4/1986 |
| EP | 0176033 | 4/1986 |
| EP | 176034 A | 4/1986 |
| EP | 0206751 | 12/1986 |
| EP | 0210929 | 2/1987 |
| EP | 0245825 | 11/1987 |
| EP | 0272921 | 6/1988 |
| EP | 0284288 | 9/1988 |
| EP | 0303915 | 2/1989 |
| EP | 0315071 | 5/1989 |
| EP | 0350846 | 7/1989 |
| GB | 2164938 | 4/1986 |
| GB | 2190378 | 11/1987 |
| WO | 8500806 | 2/1985 |
| WO | 8504652 | 10/1985 |
| WO | WO/1605 | 10/1991 |

OTHER PUBLICATIONS

Boris et al., Arch. Dermatol. Res. (1988) 280:246–251.*
Kistler, A. Carcinogenesis 7(7) pp. 1175–1182. 1986.*
A General Synthesis of Terminal and Internal Arylalkynes by the Palladium–Catalyzed Reaction of Alkynylzinc Reagents with Aryl Halides by Anthony O. King and Ei–ichi Negishi, *J. Org. Chem. 43* No. 2, 1978 p. 358.
Conversion of Methyl Ketones into Terminal Acetylenes and (E)–Tri–substituted Olefins of Terpenoid Origin, Negishi, Anthony O. King, and William L. Klima, *J. Org. Chem. 45* No. 12, 1980 p. 2526–2528.
Sporn et. al. in *J. Amer. Acad. Derm.* 15:756–764 (1986).
A Convenient Synthesis of Ethynylarenes and Diethynylarenes by S. Takahashi, Y. Kuroyama, K. Sonogashira, N. Hagihara, *Synthesis* 1980 p. 627–630.
Shudo et al. in *Chem. Phar. Bull.* 33:404–407 (1985).
Kagechika et. al. in *J. Med. Chem.* 31:2182–2192 (1988).
Chemistry and Biology of Synthetic Retinoids by Marcia I. Dawson and William H. Okamura, published by CRC Press Inc., 1990, p. 334–335, 354.
Synthesis of 2,2'–Diacyl–1,1'–biaryls. Regiocontrolled Protection of . . . by Mervic, et al, *J. Org. Chem.*, No. 45, p. 4720–4725, 1980.
A Dopamine Receptor Model and Its Application in the Design of a New Class of Rigid Pyrrolo[2,3–g]isoquinoline Antipsychotics, Gary L. Olson, et al. *American Chemical Society*, 1981, Vo. 24, No. 9, pp. 1026–1031.
6.2.3. Conformational Restriction, Williams, et al., *Drug Discovery and Development*, 1987 The Humana Press, pp. 54–55.
V. Retinoid Structure–Biological Activity Relationships, Chemistry and Biology of Synthetic Retinoids, pp. 324–356.
Characterization of Human Sebaceous Cells In Vitro, Thomas I.Doran, et al., The Journal of Investigative Dermatology, vol. 96, No. 3, Mar. 1991.
Davis et al., J. Organomettalic Chem 387 (1990) 381–390.
Organ maintenance of human sebaceous glands: in vitro effects of 13–cis retinoic acid and testesterone,John Ridden, et al., *Journal of Cell Science*, vol. 95, 1990, pp. 125–136.

* cited by examiner

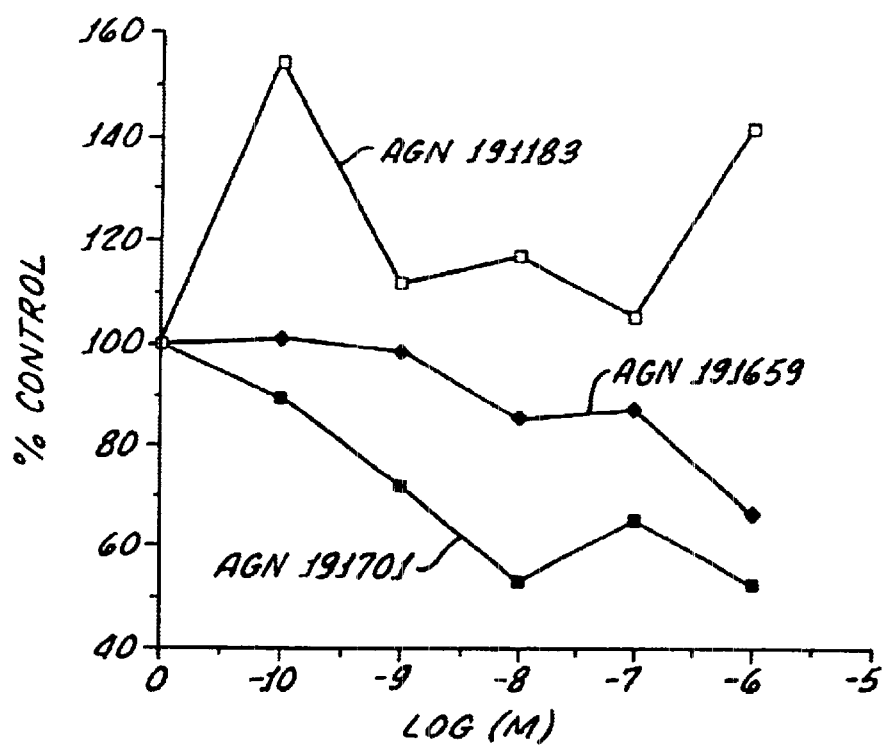
FIG. 2a.
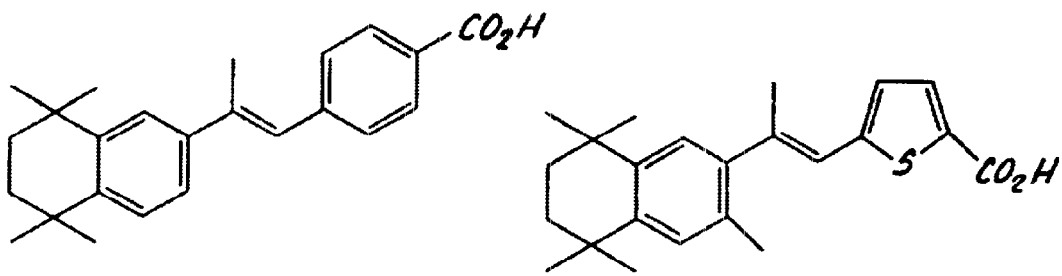
FIG. 2b.
(PRIOR ART)
FIG. 2c.
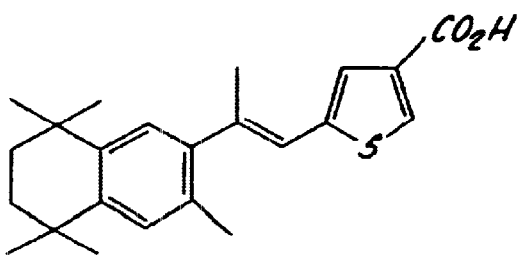
FIG. 2d.

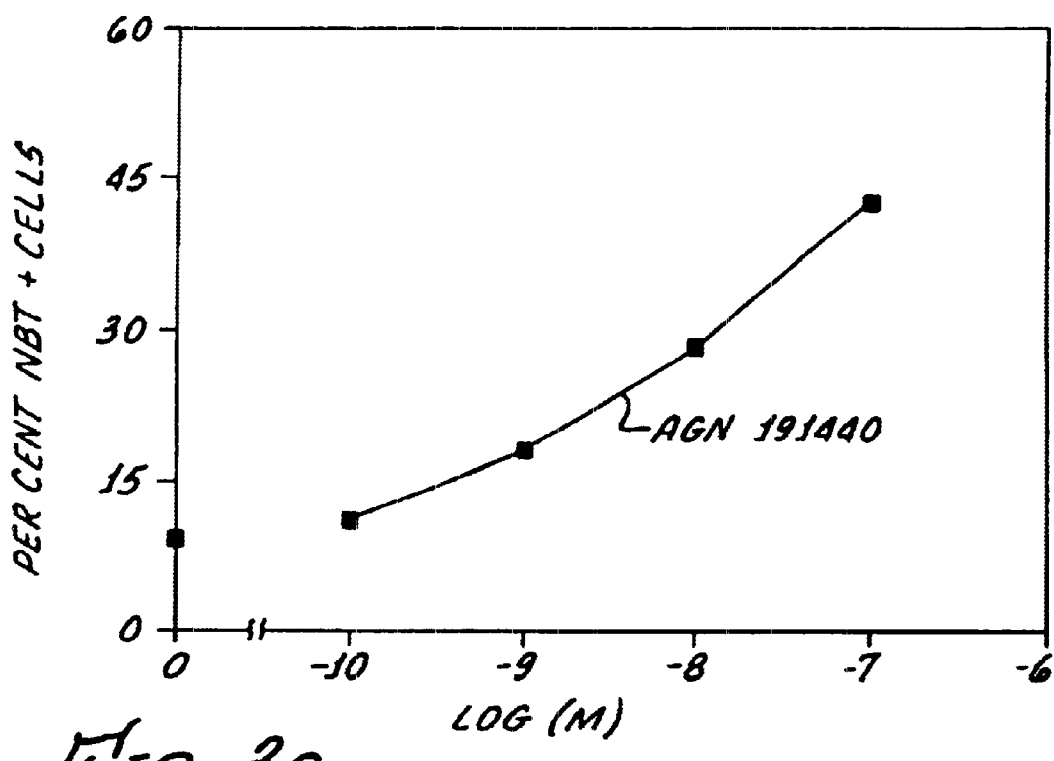
_Fig. 3a._
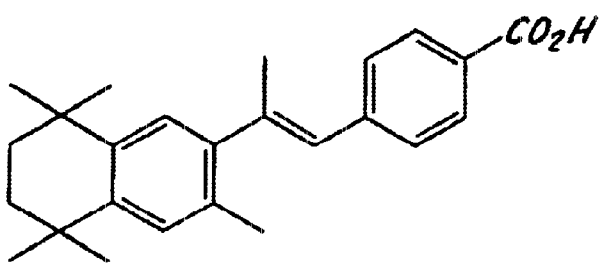
_Fig. 3b._

US 6,624,188 B1

METHOD OF TREATMENT WITH COMPOUNDS HAVING RETINOID-LIKE ACTIVITY AND REDUCED SKIN TOXICITY AND LACKING TERATOGENIC EFFECTS

CROSS-REFERENCE TO RELATED APPLICATION

The present application is a divisional of application Ser. No. 07/898,764 filed on Jun. 11, 1992, U.S. Pat. No. 5,324,840.

FIELD OF THE INVENTION

The present invention is directed to methods of administering to mammals including humans, compounds which have retinoid like activity and which lack substantial teratogenic activity and have substantially reduced skin toxicity. The present invention is also directed to pharmaceutical compositions adapted for administering said compounds having retinoid like activity, reduced skin toxicity, and lacking substantial teratogenic activity. In some instances the present invention is also directed to novel compounds having said retinoid like activity, reduced skin toxicity, and lacking teratogenic activity.

BRIEF DESCRIPTION OF THE PRIOR ART

Compounds which have retinoid like activity are well known in the art, and are described in numerous United States and foreign patents and in scientific publications. It is generally known and accepted in the art that retinoid like activity is useful for treating animals of the mammalian species, including humans, for curing or alleviating the symptoms and conditions of numerous diseases and conditions. In other words, it is generally accepted in the art that pharmaceutical compositions having a retinoid like compound or compounds as the active ingredient are useful as regulators of cell proliferation and differentiation, and particularly as agents for treating dermatoses, such as acne, Darier's disease, psoriasis, icthyosis, eczema and atopic dermatitis, and for treating and preventing malignant hyperproliferative diseases such as epithelial cancer, breast cancer, prostatic cancer, head and neck cancer and myeloid leukemias, for reversing and preventing atherosclerosis and restenosis resulting from neointimal hyperproliferation, for treating and preventing other non-malignant hyperproliferative diseases such as endometrial hyperplasia, benign prostatic hypertrophy, proliferative vitreal retinopathy and dysplasias, for treating autoimmune diseases and immunological disorders (e.g. lupus erythematosus) for treating chronic inflammatory diseases such as pulmonary fibrosis, for treating and preventing diseases associated with lipid metabolism and transport such as dyslipidemias, for promoting wound healing, for treating dry eye syndrome and for reversing and preventing the effects of sun damage to skin.

The compounds developed in the prior art with retinoid like properties, are, however, not without disadvantages. Several such prior art compounds cause serious irritation when applied to the skin (which is an important mode of application for treatment of skin conditions) and cause skin toxicity when administered orally as well. Many of the prior art compounds having retinoid like activity are teratogenic. Teratogenecity or teratogenic activity can be defined as an undesirable effect of a drug on a developing fetus. It is generally accepted in the art that pregnant females, and even females who are not pregnant but in the child-bearing age should avoid teratogenic drugs.

In light of the foregoing, there is a significant need in the prior art for pharmaceutical compositions, methods of treatment and new chemical entitities which are effective as treatment of the diseases and conditions for which retinoid like compounds are usually applied, and which have reduced or no teratogenic activity and cause no significant irritation on the skin.

With respect to specific compounds or classes of compounds having retinoid like or other biological activity, the following examples are noted.

German Patent DE 3316-932 A describes 1-phenyl-2-chromanyl-propylene derivatives and sulphur and nitrogen analogs. Specific examples of this disclosure are ethyl p-[(E)-2-(4,4-dimethyl-6-chromanyl, thiochromanyl or 1,2, 3,4-tetrahydro-6-quinolinyl)propenyl]-1-benzoate.

U.S. Pat. No. 4,826,984 describes benzopyranyl (chromanyl) and benzofuranyl-propenyl benzoic acids and esthers thereof, an example being ethyl-p-(2-(4,4-dimethyl chroman-6-yl)-propenyl benzoate.

European EP 130 795 A discloses 4,4-dimethyl-6-chromanyl alkenyl benzoic acid derivatives, thiochromanyl and tetrahydroquinolinyl analogs. The 2 and 7 positions of the chroman, thiochroman and tetrahydroquinoline ring moieties in these compounds are not substituted.

The publication WO 8500-806 A discloses 4,4.-dimethyl-chroman-6-yl and 4,4-dimethyl-thiochroman-6-yl-ethenyl and 4,4-dimethyl-chroman-6-yl and 4,4-dimethyl-thiochroman-6-yl- propenyl benzoic acid, its esters and the corresponding thiophencarboxylic acid and other heterocyclic acid analogs. The 2 position of the chroman or thiochroman ring is unsubstituted.

The publication EP 350 846 A discloses p-(2-(3,4-dihydro-4,4-dimethyl-dihydrochroman-7-yl)-propeneyl] benzoic acid ethyl ester and related compounds, The publication WO 8504 652 A discloses certain diaryl substituted propenyl compounds, an example being ethyl (E)-4-[2-(4-isopropylphenyl)-propenylbenzoate.

European patent EP 206 751 A discloses 2-substituted phenyl-alkenyl-quinoline derivatives as inhibitors of leukotriene synthesis. An examples of a compound of this reference are (E)-4-(3-(2-(quinolin-2-yl)-1-methylethenylphenoxy)butyric acid.

Published European patent application 0 098 591 A1 describes rodenticidal disubstituted propenyl compounds, an example of which is ethyl p-[2-(4,5,6,7-tetrahydro-4,4,7,7-tetramethylbenzo[b]thien-2-yl)propenyl benzoate, and another example is ethyl 6-[(E)-2-(4,5,6,7-tetrahydro-4,4,7, 7-tetramethylbenzo[b]thien-2-yl)propenyl]nicotinate.

Great Britain Patent GB 2190-378 describes tetramethyl-tetrahydronaphthylpropenylphenol compounds, examples of which are ortho, meta or para (E)-2-(5,6,7,8-tetrahydro-5,5, 8,8-tetramethyl-2-naphthyl)propenyl)phenol.

German Patent DE 3602-473 A discloses aralkenyl-phenol derivatives, examples of which are (E)-1-(4-hydroxyphenyl)-2-(5,6,7,8-tetrahydro-5,5,8,8-tetramethyl-2-naphthyl)propene and (E)-1-(4-methoxyphenyl)-2-(5,6,7, 8-tetrahydro-5,5,8,8-tetrameth-yl-2-naphthyl)propene.

European Patent EP 176 033 A discloses isoxazolyl-vinyl indane and tetrahydronaphthalene derivatives, an example of which is (E)-5-[2-(3-fluoro-5,5,8,8-tetramethyl-5,6,7,8-tetrahydro-2-naphthyl)-1-propenyl]-isoxazole-3-carboxylic acid.

The publication EP 303 915 discloses indanyl and tetrahydronaphthyl and substituted phenyl propenes as retinoids, where the phenyl substituent is sulfur substitited.

An example of the disclosed compounds is methyl 4-(2-(5,6,7,8-tetrahydro-5,5,8,8-tetramethyl-2-naphthyl(propenyl)phenylsulphone.

European patent EP 176 032 A discloses 6-styryl-tetrahydro-naphthalene derivatives, examples of which are (E)-4-[2-(5,6,7,8-tetrahydro-5,5,8,8-tetramethyl-7-hydroxy-2-naphthalenyl)-1-propenyl]benzylalcohol, and E-4-[2-(5,8-dihydro-5,5,8,8-tetramethyl-2-naphthalenyl)-1-propenyl]benzoic acid.

European Patent EP 315 071 discloses 1-benzocycloheptenyl-2-carboxy-phenyl ethylene derivatives, an example of which is ethyl p-(E)-2-(6,7,8,9-tetrahydro-7,7-dimethyl-5H-benzocycloheptene-2-yl)propenyl benzoate.

German Patent DE 3524-199-A discloses stilbene-4-carboxylic acid derivatives, examples of which are [E-2-(3,4-diisopropylphenyl)propenyl]benzoic acid, [E-2-(3-tert-butylphenyl)propenyl]benzoic acid.

European Patent EP 245 825 describes heterocyclyl-alkenyl benzene derivatives, examples of which are 3-(β-(4'-hydroxy-3'-methoxyphenyl)ethenyl)-5-methylpyrazole and 5-(β(4'-hydroxy-3',5'-bis-(1,1-dimethylethyl)phenyl)-ethenyl)-5-methylpyrazole.

European Patent EP 210 929 A discloses certain 2-aryl-naphthalene derivatives useful in dermatological and ophthalmologycal medicaments. Intermediates leading to the synthesis of these compounds include certain arylethenyl benzene derivatives.

German Patent DE 3531 722 A discloses certain benzonorbornene derivatives which have vitamin A like activity.

Great Britain patent GB 2164-938 A discloses certain 2-styryl-naphthalene derivatives having retinoid like activity. An example of the compounds is 2-(4-methyl-β-methyl-styryl)naphthalene.

U.S. Pat. No. 4,326,055 discloses ethene derivatives which have a substituted phenyl ring and a substituted indane or tetrahydronaphtalene group. The compounds are described as tumor inhibiting agents, and useful for treating dermatological conditions and rheumatic illnesses.

U.S. Pat. No. 4,723,028 discloses 1,2-diphenylethene (stilbene) derivatives which have retinoid like activity.

U.S. Pat. No. 4,740,519 discloses certain aromatic heterocycle derivatives which have retinoid like activity.

Published European Patent Application 0130795 discloses ethene derivatives, where the ethene moiety is substituted by a substituted phenyl group and by a substituted chroman, thiochroman or quinoline group. The compounds are useful for inhibiting the degradation of cartilage in mammals.

Several co-pending applications and recently issued patents of the present inventor, which are assigned to the assignee of the present application, are directed to further compounds having retinoid like activity.

SUMMARY OF THE INVENTION

It has been discovered in accordance with the present invention that the partial structure or moiety shown in Formula 1 below, imparts significantly reduced teratogenic activity, and reduces skin toxicity in a class of disubstituted ethene compounds which have retinoid like or related biological activity.

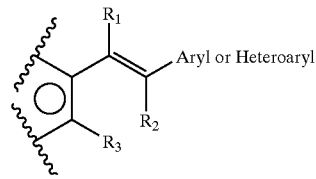

Formula 1

In Formula 1 the partially drawn ring signifies an aromatic ring which may be carbocyclic or heteroaromatic, 6-membered or 5-membered, and may be condensed with another ring as particularly described below. $R_1$ is lower alkyl, Cl, Br, or I, $R_2$ is H, lower alkyl, Cl, Br, or I, and $R_3$ is lower alkyl, Cl, Br, I, or is an ether, thioether, ester, thioester, amine or substituted amine group. It is an important feature of the present invention that the ethene moiety (double bond) is connected to an aromatic ring where the aromatic carbon adjacent to the carbon directly connected to the double bond (in other words the carbon in the ortho position) has a substituent ($R_3$) with some steric bulk (other than hydrogen) and that the carbon of the olefinic double bond which is attached to the ortho substituted aromatic ring is also substituted with a substituent ($R_1$) other than hydrogen.

In light of the foregoing, the present invention covers a method of treating animals of the mammalian species, including humans, and particularly females of child-bearing age and pregnant females, with a non-teratogenic pharmaceutical composition comprising one or more compounds of Formula 2 or of Formula 3 as the active ingredient, for treatment of the diseases or conditions against which retinoid like compounds are useful, namely as regulators of cell proliferation and differentiation, and particularly as agents for treating dermatoses, such as acne, Darier's disease, psoriasis, icthyosis, eczema and atopic dermatitis, and for treating and preventing malignant hyperproliferative diseases such as epithelial cancer, breast cancer, prostatic cancer, head and neck cancer and myelorid leukemias, for reversing and preventing atherosclerosis and restenosis resulting from neointimal hyperproliferation, for treating and preventing other non-malignant hyperproliferative diseases such as endometrial hyperplasia, benign prostatic hypertrophy, proliferative vitreal retinopathy and dysplasias, for treating autoimmune diseases and immunological disorders (e.g. lupus erythematosus, for treating chronic inflammatory diseases such as pulmonary fibrosis, for treating and preventing diseases associated with lipid metabolism and transport such as dyslipidemias, for promoting wound healing, for treating dry eye syndrome and for reversing and preventing the effects of sun damage to skin.

The present invention is also directed to the pharmaceutical compositions used in the above-noted methods of treatment.

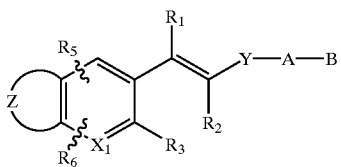

Formula 2

The present invention particularly covers methods for treating diseases and conditions where retinoid like compounds are effective for treatment, but their use is limited because of their generally known skin toxicity.

Formula 3

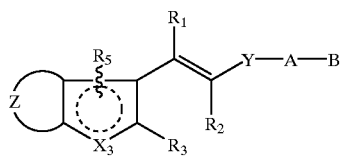

In Formula 2 the symbols are defined as follows:

$R_1$ is lower alkyl, Cl, Br, or I;

$R_2$ is H, lower alkyl, Cl, Br, or I;

$R_3$ is lower alkyl, Cl, Br, I, $OR_{11}$, $SR_{11}$, $OCOR_{11}$, $SCOR_{11}$, $NH_2$, $NHR_{11}$, $N(R_{11})_2$, $NHCOR_{11}$, or $NR_{11}$—$COR_{11}$;

$R_5$ and $R_6$ independently are H, lower alkyl, Cl, Br, I, lower alkoxy or lower thioalkoxy of 1 to 6 carbons, or $R_6$ is absent;

A is $(CH_2)_n$ where n is 0–5, lower branched chain alkyl having 3 to 6 carbons, cycloalkyl having 3 to 6 carbons, alkenyl having 2 to 6 carbons and 1 or 2 double bonds, alkynyl having 2 to 6 carbons and 1 or 2 triple bonds;

B is hydrogen, COOH or a pharmaceutically acceptable salt thereof, $COOR_8$, $CONR_9R_{10}$, $-CH_2OH$, $CH_2OR_{11}$, $CH_2OCOR_{11}$, CHO, $CH(OR_{12})_2$, $CHOR_{13}O$, $-COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5 to 10 carbons, or phenyl or lower alkylphenyl, $R_{11}$ is alkyl of 1 to 10 carbons, phenyl or lower alkylphenyl, $R_{12}$ is lower alkyl, and $R_{13}$ is divalent alkyl radical of 2–5 carbons;

$X_1$ is $CR_5$ or N, and in case $X_1$ is N it can be located in any unsubstituted position of the 6-membered aromatic ring;

Y is phenyl, thienyl, furyl, pyrrolyl, pyridyl, pyrimidyl, pyrazinyl, pyridazinyl, thiazolyl, imidazolyl and oxazolyl, and Z represents independently H, or one or two substituents being lower alkyl, lower alkoxy, lower thioalkoxy, lower alkenyl having one or more double bonds, lower alkenyloxy having one or more double bonds, or lower thioalkenyloxy having one or more double bonds, or Z represents $-(CR_{14})_4-$, or Z represents $-(CR_{14})=(CR_{14})-C(R_{14})_2-$, or Z represents $-(CR_{14})_3-N-$, or Z represents $-(CR_{14})=(CR_{14})-X_2-$, or Z represents $-C(R_{14})_2-C(R_{14})_2-X_2-$, or Z represents $-C(R_{14})_2-CR_{14}=CR_{14}-X_2-$, or Z represents $-C(R_{14})_2-C(R_{14})_2-C(R_{14})_2-C(R_{14})_2-$, or Z represents $-C(R_{14})_2-C(R_{14})_2-C(R_{14})_2-X_2-$ where $R_{14}$ independently is H, lower alkyl, lower alkoxy, lower thioalkoxy, Cl, Br, or I, $X_2$ is O, S, or $NR_{15}$ and $R_{15}$ is H or lower alkyl.

In Formula 3 the symbols $R_1$, $R_2$, $R_3$, $R_5$, Y, A, B, and Z are defined as in connection with Formula 2, or $R_5$ may be absent; the dashed circle in the 5 membered ring indicates the presence of two double bonds in the membered ring, and $X_3$ is O, S, NH or N-lower alkyl, and the $X_3$ group can be located in any unsubstituted position of the 5-membered aromatic ring.

New chemical compounds of the present invention are characterized by Formula 4, 5 and 6.

Formula 4

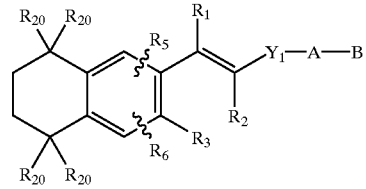

In Formula 4 $R_1$, $R_2$, $R_3$, $R_5$, $R_6$, A and B are defined as in connection with Formula 2.

$R_{20}$ is independently H or lower alkyl, and $Y_1$ is thienyl, furyl or pyridyl.

Formula 5

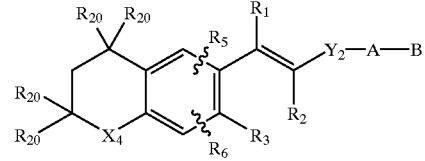

In Formula 5 $R_1$, $R_2$, $R_3$, $R_5$, $R_6$, A and B are defined as in connection with Formula 2; $R_{20}$ is defined as in Formula 4;

$Y_2$ is phenyl, thienyl, furyl or pyridyl, and $X_4$ is S, O, NH or N-lower alkyl.

Formula 6

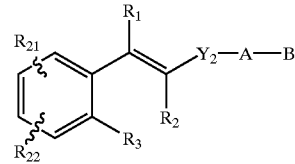

In Formula 6 $R_1$, $R_2$, $R_3$, A and B are defined as in connection with Formula 2;

$Y_2$ is phenyl, thienyl, furyl or pyridyl, and $R_{21}$ and $R_{22}$ are H or lower alkyl, with the proviso that both of these substituents are not H.

BRIEF DESCRIPTION OF THE DRAWING FIGURES

FIG. 2 is graph showing as percentage of control, the incorporation of $^3H$-thymidine (a measure of DNA synthesis) as a function of concentration of test compounds and a reference compound. The X-axis plots molar concentration of retinoid compounds on a logarithmic scale.

FIG. 3 is a graph showing the results of the HL 60 Cell NBT Reduction (cell differentiation) assay with compound AGN 191440 (Compound 11).

GENERAL EMBODIMENTS

Definitions

Figure 1A:
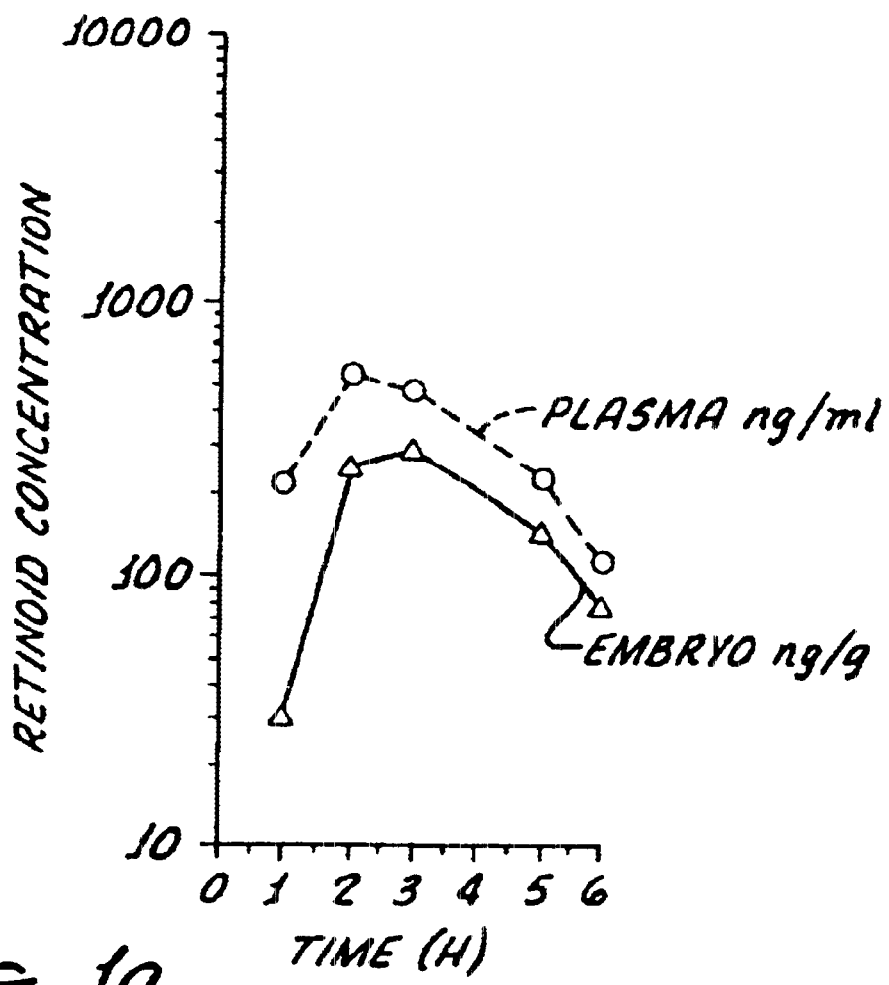
FIG. 1 is a graph showing the concentration of compound AGN 191701 in nanograms per ml, or nanograms per gram as indicated on the chart, in the plasma and embryo of mice at various times after oral intubation of a single dose of 10 mg/kg of the compound.

The term alkyl refers to and covers any and all groups which are known as normal alkyl, branch-chain alkyl and cycloalkyl. The term alkenyl refers to and covers normal alkenyl, branch chain alkenyl and cycloalkenyl groups having one or more sites of unsaturation. Lower alkyl means the above-defined broad definition of alkyl groups having 1 to 6 carbons, and as applicable, 3 to 6 carbons for branch chained and cyclo-alkyl groups. Lower alkenyl is defined similarly having 2 to 6 carbons for normal alkenyl, and 3 to 6 carbons for branch chained and cycloalkenyl groups.

The term "ester" as used here refers to and covers any compound falling within the definition of that term as classically used in organic chemistry. Where B (of Formula 2, 3, 4, 5 and 6) is —COOH, this term covers the products derived from treatment of this function with alcohols, preferably with aliphatic alcohols having 1–6 carbons. Where the ester is derived from compounds where B is —CH$_2$OH, this term covers compounds of the formula —CH$_2$OOCR$_{11}$ where R$_{11}$ is any substituted or unsubstituted aliphatic, aromatic or aliphatic-aromatic group, preferably with 1–6 carbons in the aliphatic portions.

Preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids or alcohols. Also preferred are the phenyl or lower alkylphenyl esters.

Amide has the meaning classically accorded that term in organic chemistry. In this instance it includes the unsubstituted amides and all aliphatic and aromatic mono-and di-substituted amides. Preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from lower alkyl amines. Also preferred are mono- and di-substituted amides derived from the phenyl or lower alkylphenyl amines. Unsubstituted amides are also preferred.

Acetals and ketals include the radicals of the formula —CK where K is (—OR)$_2$. Here, R is lower alkyl. Also, K may be —OR$_1$O— where R$_1$ is lower alkyl of 2–5 carbon atoms, straight chain or branched.

A pharmaceutically acceptable salt may be prepared for any compound used in the method of treatment of this invention, if the compound has a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The compounds utilized in accordance with the method of treatment of the present invention, as well as those compounds of the present invention which comprise novel composition of matter, contain at least one double bond and therefore may have trans and cis (E and Z) isomers. In addition, some of the compounds used in the method of treatment of the present invention may contain one or more chiral centers and therefore exist in enantiomeric and diastereomeric forms. The scope of the present invention is intended to cover all such isomers per se, as well as mixtures of cis and trans isomers, mixtures of diastereomers and racemic mixtures of enantiomers (optical isomers) as well.

Methods of Administration

The compounds used in the method of treatment of this invention may be administered systemically or topically, depending on such considerations as the condition to be treated, need for site-specific treatment, quantity of drug to be administered, and similar considerations.

In the treatment of dermatoses particularly, topical administration may be used, though in certain cases such as treatment of severe cystic acne, oral administration may be preferred. Any common topical formulation such as a solution, suspension, gel, ointment, or salve and the like may be used. Preparation of such topical formulations are well described in the art of pharmaceutical formulations as exemplified, for example, by *Remington's Pharmaceutical Science*, Edition 17, Mack Publishing Company, Easton, Pa. For topical application, these compounds could also be administered as a powder or spray, particularly in aerosol form.

If the drug is to be administered systemically, it may be confected as a powder, pill, tablet or the like, or as a syrup or elixir for oral administration. For intravenous or intraperitoneal administration, the compound will be prepared as a solution or suspension capable of being administered by injection. In certain cases, it may be useful to formulate these compounds in suppository form or as an extended release formulation for deposit under the skin or intermuscular injection.

Other medicaments can be added to such topical formulation for such secondary purposes as treating skin dryness, providing protection against light; other medications for treating dermatoses, preventing infection, reducing irritation, inflammation and the like.

Treatment of dermatoses or any other indications known or discovered to be susceptible to treatment by retinoid like compounds will be effected by administration of the therapeutically effective dose of one or more compounds in accordance with the instant invention. A therapeutic concentration will be that concentration which effects reduction of the particular condition, or retards its expansion. In certain instances, the drug potentially could be used in a prophylactic manner to prevent onset of a particular condition. A given therapeutic concentration will vary from condition to condition and in certain instances may vary with the severity of the condition being treated and the patient's susceptibility to treatment. Accordingly, a given therapeutic concentration will be best determined at the time and place through routine experimentation. However, it is anticipated that in the treatment of, for example, acne, or other such dermatoses, that a formulation containing between 0.001 and 5 percent by weight, preferably about 0.01 to 1% will usually constitute a therapeutically effective concentration. If administered systemically, an amount between 0.01 and 100 mg per kg body weight per day, but preferably about 0.1 to 10 mg/kg, will effect a therapeutic result in most instances.

Biological Activity

The compounds used in the method of treatment of the present invention have no teratogenic activity, or are substantially less teratogenic than comparable prior art compounds. The lack of teratogenicity of these compounds is demonstrated by an in vivo teratology study involving gestating ICR mice. The methodology of the study is described as follows:

Animals

ICR mice (Ace Animals, Boyertown, Pa.) were used. Mature male and virgin female ICR mice were housed in environmentally controlled rooms and acclimatized to a 12 hour light/dark cycle (light cycle 6 A.M. to 6 P.M.) for 2 weeks prior to use. All animals were maintained on Purina Lab Chow and tap water ad libitum. A group of 3–4 females was caged with a single male of proven fertility for 4 hours. Presence of a vaginal plug immediately afterward was regarded as evidence of successful mating, and this day was designated as day 0 of gestation.

Teratology

A single oral dose (0.1, 1.0, 10 or 100 mg/kg) of the test drug was administered on the morning (10 A.M.) of day 11 of gestation. All animals were killed by cervical dislocation under mild ether anesthesia on day 17 of gestation. Upon laparotomy, the fetuses were examined for external malformations and weighed; one-half of each litter was then fixed in 95% ethanol and processed for staining of the skeleton by the rapid, alizarin red-S dye method. These preparations were examined under a dissection microscope to screen for abnormalities in the axial and the appendicular skeleton. The other half of each litter was fixed in Bouin's solution and examined by freehand razor serial sectioning to screen for anomalies of the brain, face, and palate.

Differences in dose-related incidence of malformations and resorptions were assessed by computing percentages of affected conceptuses among total implantation sites. The groups were compared statistically by a method based on Student's t-tests of arcs in square root transformed percentages. Values at 0.05 probability level were considered significant. The median effective dose was calculated by logarithmic curve fitting of the dose-response data.

TABLE 1

| Compound | Dose (mg/kg) | # Litters Treated | # Litters Normal | % Re-sorbed | Teratogenic Effects | |
|---|---|---|---|---|---|---|
| | | | | | % Cleft Palate | % Limb Defects |
| AGN 191440 | 1 | 7 | 5 | 19 | 13 | 17 |
| (Compound 11) | 10 | 8 | 1 | 2 | 88 | 75 |
| | 100 | 3 | 0 | 100 | — | — |
| AGN 191183 | 0.01 | 5 | 2 | 3 | 29 | 20 |
| (prior art) | 0.1 | 4 | 0 | 30 | 100 | 100 |
| | 1 | 2 | 0 | 100 | — | — |
| | 10 | 2 | 0 | 100 | — | — |
| AGN 191701 | 1 | 1 | 1 | 18 | 0 | 0 |
| (Compound 19) | 10 | 3 | 3 | 14 | 0 | 0 |
| | 100 | 3 | 2 | 2 | 19 | 22 |

Results of the study are indicated in Table 1. As it can be seen from Table 1, The compound designated AGN 191183 is a prior art compound having the structure shown by Formula 7. The compound of Formula 7 does not have the moiety required for reduced teratogenecity (or lack of teratogenecity) as required in accordance with he present invention and shown for example, in Formula 1. The data for this compound indicate significant teratogenecity; when the compound was given in a single dose of 0.1 mg/kg all the litters (100%) exhibited teratogenic effects. In contrast with the foregoing, two examplary compounds of the present invention (Compound AGN 191440 also designated in this application as Compound 11 and AGN 191701 also designated in this application as Compound 19) are significantly less teratogenic. Compound AGN 191440 was approximately 100 times less teratogenic than AGN 191183, (for example AGN 191440 at 1 mg/kg produced less teratogenic effects than AGN 191183 at 0.01 mg/kg) and AGN 191701 was approximately $10^4$ times less teratogenic than AGN 191183 (for example AGN 191701 at 100 mg/kg produced less teratogenic effects than AGN 191183 at 0.01 mg/kg).

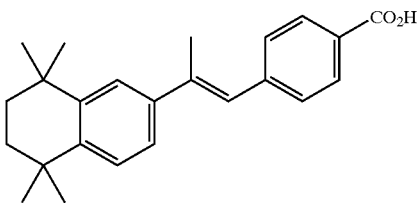

Formula 7

In an in vitro bioassay which measures inhibition of chondrogenesis (bone formation) in chick embryo cells as a classic measure of teratogenecity the results shown in Table 2 were obtained. The assay is described as follows:

High-density "spot" cultures of limb bud mesenchymal cells were used to compare the ability of various concentrations of test drugs to suppress chondrogenic differentiation as a bioassay. Forelimb buds of mouse embryos on day 12 of gestation (54±2 somites) were dissociated in a trypsin-EDTA solution, and the resultant single-cell suspension was plated as 20-µl spots (200,000 cells/spot) on plastic culture dishes. Retinoid concentrations ranging from 0.3 ng/ml to 3 µg/ml (1 nM–10 µM) were added to the culture medium (Eagle's MEM+10% fetal bovine serum, GIBCO) 24 hours after initial plating. Control cultures received only the vehicle (ethanol, concentration ≦1% by vol); Retinoic acid was used as a positive control in another set of cultures.

The cultures were terminated 96 hours after plating, at which time the medium was removed and the cells were fixed for 1 hour in 10% formalin containing 0.5% cetylpyridinium chloride. The cultures were rinsed in acetic acid and stained for 1 hour in 0.5% Alcian blue solution at pH 1.0, differentiated in 3% acetic acid, and then dehydrated in ethanol and scored for chondrogenesis under the microscope. An absence or reduction in the number of cartilage nodules in stained cultures as compared with control cultures was taken as a measure of suppression of chondrogenesis. The number of cartilage nodules stained in the whole spot, mean number of nodules, and standard deviations were calculated for four replicate cultures per treatment. The median concentration causing a 50% inhibition of chondrogenesis compared with controls ($IC_{50}$) was calculated by logarithmic curve fitting of the dose-response data.

As it can be seen in Table 2, the prior art compound AGN 191183 had an $IC_{50}$ concentration (concentration which inhibited chondrogenesis by 50%) which is approximately 1000 times less than the $IC_{50}$ of compound AGN 191440 in accordance with the invention, and approximately 6,000 times less than compound AGN 191701 in accordance with the invention. Thus, the prior art compound AGN 191183 was demonstrated to be significantly more potent as a teratogen than the compounds in accordance with the invention.

TABLE 2

| Compound | $IC_{50}$ (Mg/ml) |
| --- | --- |
| AGN 191183 (prior art) | 0.003 |
| AGN 191440 (Compound 11) | 2.5 |
| AGN 191701 (Compound 19) | 19.0 |

Figure 1B:
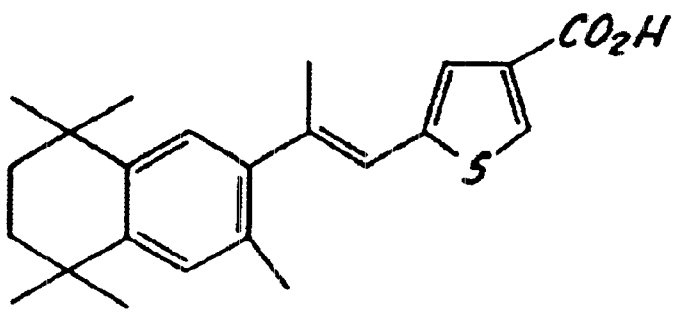

A pharmacokinetic study involving the oral intubation of mice with a 10mg/kg dose of compound AGN 191701 in accordance with the present invention, and subsequent measurement of the concentration of the drug in the maternal plasma and in the embryo, as shown in FIG. 1, reveals that compound AGN 191701 (Compound 19) is in fact present in substantial concentration in the maternal plasma and in the embryo. Yet, as the data of Table 1 show this compound has very little teratogeneic effect. In contrast, the teratogenecity of prior art compound AGN 191183 is so high that even an undetectably low concentration of the drug already causes defective embryos.

The retinoid like activity of the compounds used in accordance with the method of treatment of the present invention and of the novel compounds of the invention can be confirmed by several assay procedures. An assay involving human sebocyte cultures measures the inhibition of $^3$H-thymidine into cells, and thus measures inhibition of DNA synthesis and thus an anti-proliferative effect on sebocyte (i.e. a sebostatic effect). This assay is also considered a specific assay for effectiveness of a compound as a potential anti-acne drug. The test is conducted as follows.
Source of Skins:
Face-lift or forehead reduction skins from cosmetic surgeries were used as sources of human sebaceous gland cells (sebocytes).
Isolation of Sebocytes:
Isolated sebocytes were plated in type 1 collagen coateddishes in DMEM/F12 (1:1) medium supplemented with 8% fetal bovine serum, 2% human serum, 10 ng/ml epidermal growth factor, 1 nM cholera toxin, 1 µM hydrocortisone, and penicillin/streptomycin/amphotericin B. Secondary cultures were prepared by plating Dispase dissociated cells in collagen coated 24-well plates.

Proliferation Studies ($^3$H-thymidine Incorporation):
Sub-confluent secondary cultures were treated with the test compounds or ethanol vehicle every 2–3 days for 8 days in the above medium from which the total serum concentration was reduced to 2% and hydrocortisone was not included. During the last 6 hours of treatment, the cultures were labeled with 2 µCi/ml $^3$H-thymidine. DNA from the cells were extracted by thichoroacetic acid and perchloric acid, and assayed for radioactivity by scintillation counting and for content of DNA by the diphenylamine calorimetric method. The results were expressed as CPM/µg DNA, or as per cent of vehicle control which incorporated about 1,000–1,500 cpm/µg DNA.

As the graph of FIG. 2 shows, depicting the results of this test for compounds AGN 191701 (Compound 19), AGN 191659 (Compound 21) and for prior art compound AGN 191183, the prior art compound is not effective in this assay, whereas the examplary compounds of the invention are effective.

Other assays in which the retinoid like activity of the compounds used in accordance with the invention are confirmed are the HL-60 transglutaminase induction and HL-60 differentiation assay, the procedures of which are described as follows.
Differentiation: HL-60 Cells Nitroblue Tetrazolium Reduction Assay (NBT Reduction Assay)
HL-60 cells were grown as a suspension culture in T-162 $CM^2$ flasks in serum-free RPMI 1640 medium supplemented with insulin (5 µg/ml), transferrin (5 µg/ml), and selenium (3 nM). The cells ($1\times10^5$/well in 24-well dishes) were treated with serial dilutions of test compounds in the above RPMI 1640 medium which was additionally supplemented with 0.2 mM dibutyryl cyclic adenosine monophosphate, a component found to be necessary for efficient differentiation of the cells. Ethanol was used in the vehicle control cultures. After 3 days of incubation at 37° C. in a 5% $CO_2$ incubator, nitroblue tetrazolium (NBT) and tetradecanoylphorbol acetate (TAP), at final concentrations of 0.1% and 100 ng/ml, respectively, were mixed with the cells and incubated at room temperature for 15 to 30 minutes. Differentiated HL-60 cells acquired a purple deposit of formazan (NBT positive cells) from the reduction of NBT. The cells were then fixed in 10% paraformaldehyde and pelleted by centrifugation. The cell pellets were resuspended in a small volume of phosphate buffer saline. The number of NBT positive cells and the total number of cells of each cell suspension was determined by counting in a hemacytometer. The mean of quadruplicate cultures was expressed as per cent of NBT positive cells.

Figure 4A:
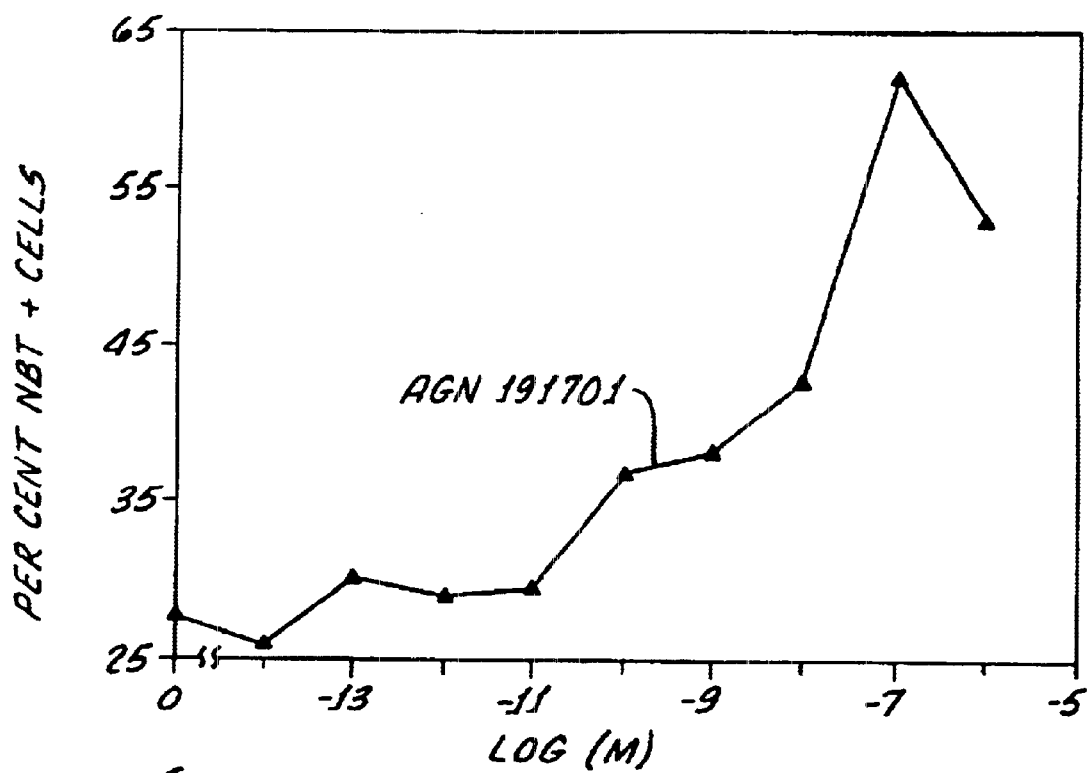
FIG. 4 is a graph showing the results of the HL 60 Cell NBT Reduction (cell differentiation) assay with compound AGN 191701 (Compound 19).
Figure 4B:
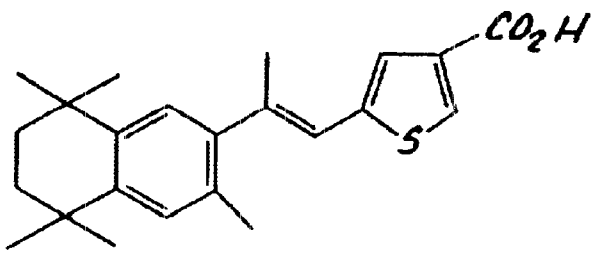
Figure 5A:
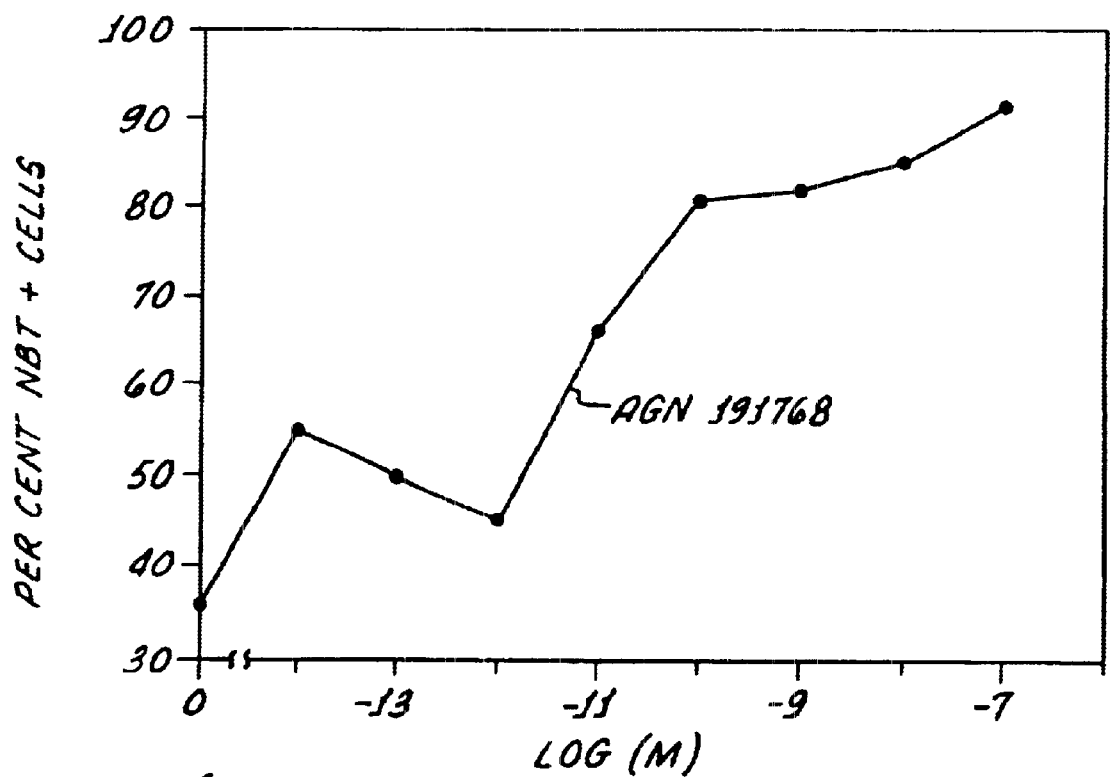
FIG. 5 is a graph showing the results of the HL 60 Cell NBT Reduction (cell differentiation) assay with compound AGN 191768 (Compound 15).
Figure 5B:
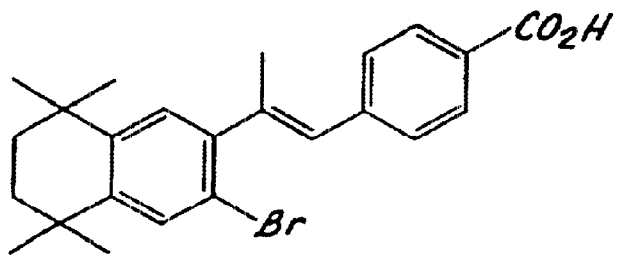

As it will be readily understood by those skilled in the art, differentiation of cells in this assay is a marker of useful retinoid like activity. The results of this assay for compounds AGN 191440 (Compound 11); AGN 191701 (Compound 19), and AGN 191768 (Compound 15) are shown in the graphs of FIGS. 3 through 5, respectively.
Tissue Transglutaminase Assay (tTGASE) in HL-60 Cells
HL-60 cells were grown as a suspension culture in T-162 $cm^2$ flasks in serum-free RPMI 1640 medium supplemented with insulin (5 µg/ml), transferrin (5 µg/ml), and selenium (3 nM). The cells ($1\times10^6$ cells/well, in 6-well dishes) were treated with serial dilutions of test compounds in the above RPMI 1640 medium which was additionally supplemented with 1 nM dibutyryl cyclic adenosine monophosphate, a component found to be necessary for efficient differentiation of the cells. Ethanol was used in the vehicle control cultures. After 1 days of incubation at 37° C. in a 7.5% $CO_2$ incubator, the cells were collected in a set of tubes and pelleted by centrifugation. The cells were lyzed in a buffer containing 20 mM Tris-HCl, pH 7.5, 1 mM EDTA, and 0.5% Triton X-100. An aliquot of the cell lysate was assayed for tTGASE activity in a reaction mixture containing 20 mM Tris-HCl, pH 7.5, 5 mM $CaCl_2$, 2 mg/ml dimethylcasein, 15 mM B-mercaptoethanol and 50 $\mu$Ci/ml [2,3-$^3$H] putrescine dihydrochloride. The reaction was carried out for 60 minutes in a 37° C. shaking water bath. The reaction was stopped by an addition of 10% trichloroacetic acid containing 0.1% putrescein. An aliquot of the stopped reaction mixture was spotted on Whatman 3 MM filter discs. The filter discs, along with the control blank filter discs, were washed twice with 5% trichloroacetic acid containing 0.1% putrescein and twice with methanol. After drying under a heat lamp, the radioactivity in the filter discs was determined by scintillation counting. An aliquot of the cell lysates was also assayed for protection concentration by the Bradford method (Bio-Rad). After subtracting the radioactivity from the control blank filter discs, the data were calculated and expressed as pmol/min/mg protein.

Figure 6A:
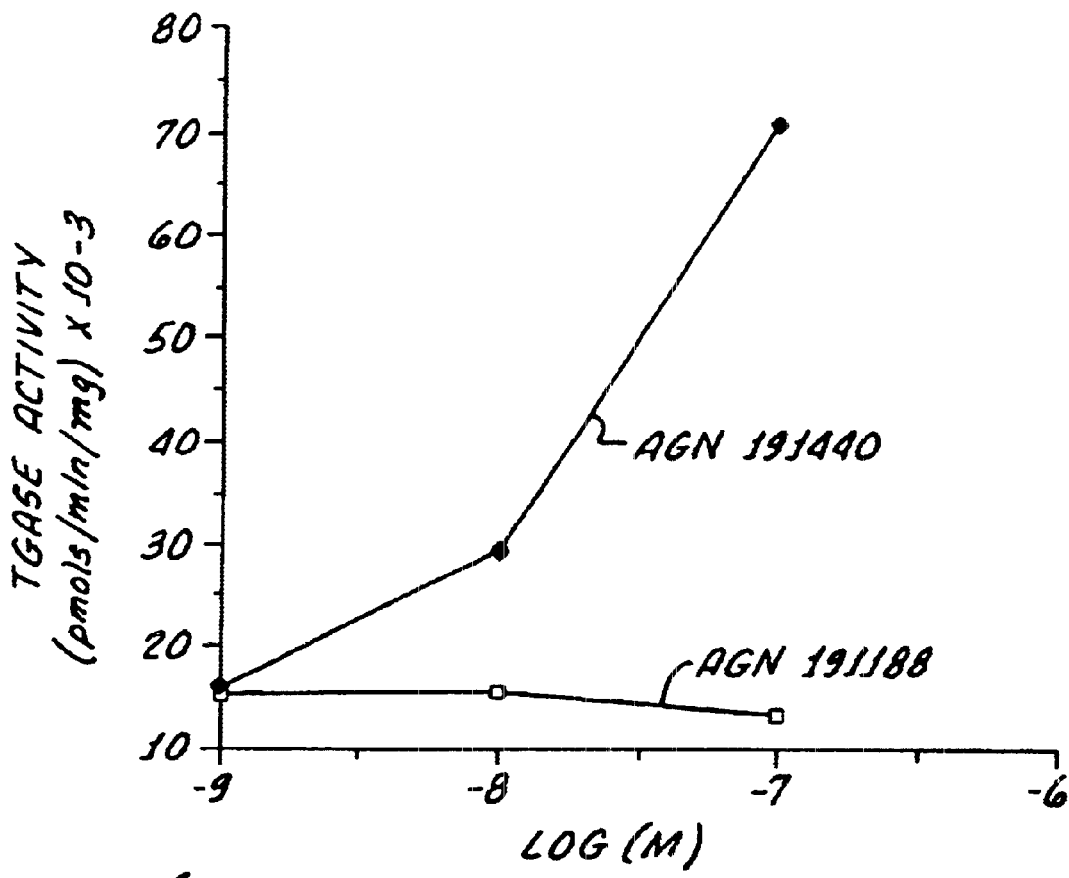
FIG. 6 is a graph showing the results of the HL 60 Cell transglutaminase assay for prior art compound AGN 191183 and also for AGN 191440 (Compound 11).
Figure 6B:
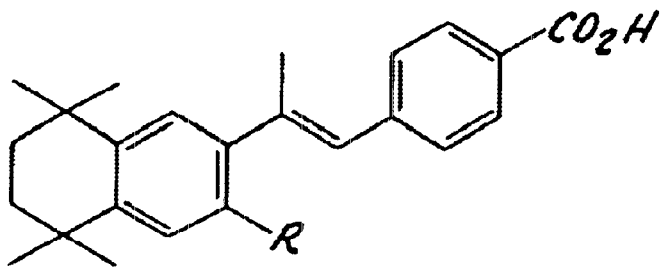
Figure 7A:
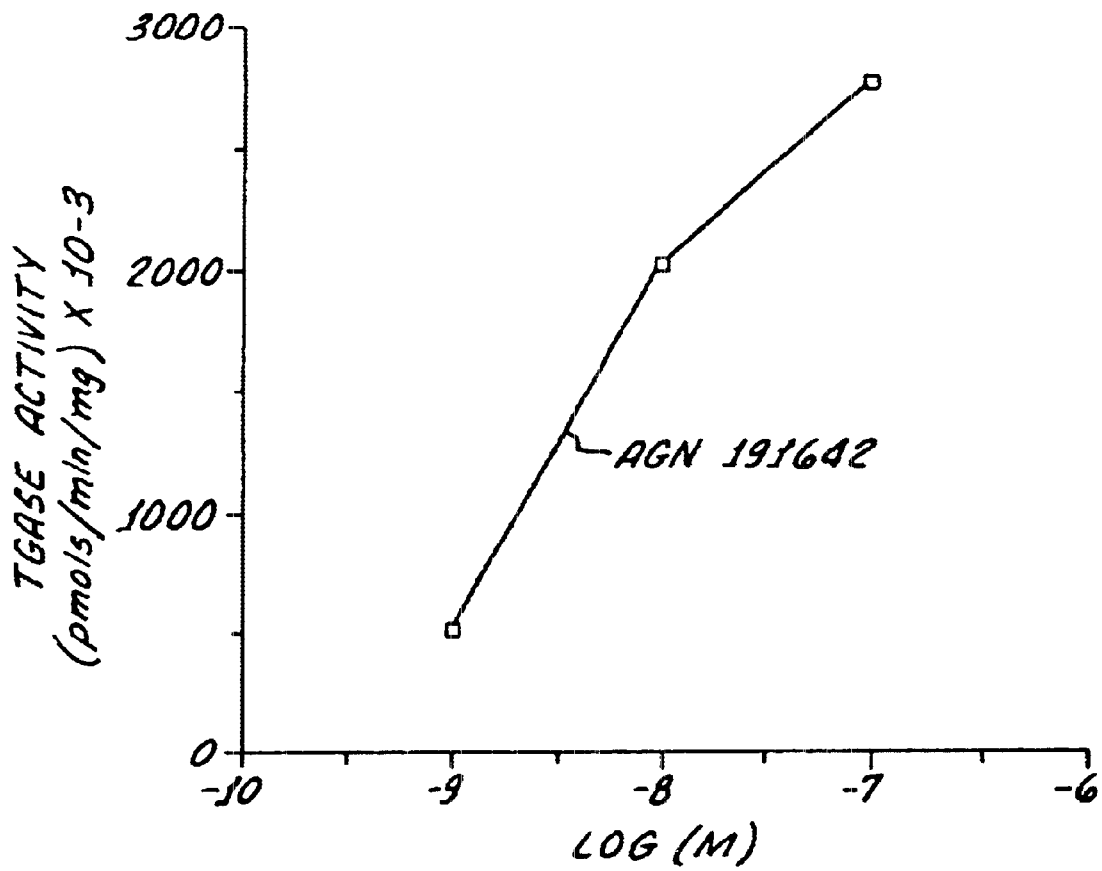
FIGS. 7 is a graph showing the results of the HL 60 Cell transglutaminase assay for AGN 191642 (Compound 13).
Figure 7B:
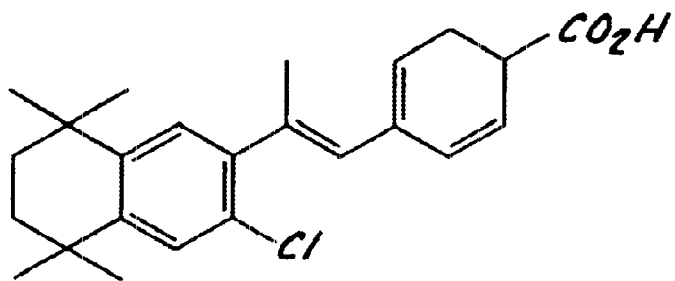
Figure 8A:
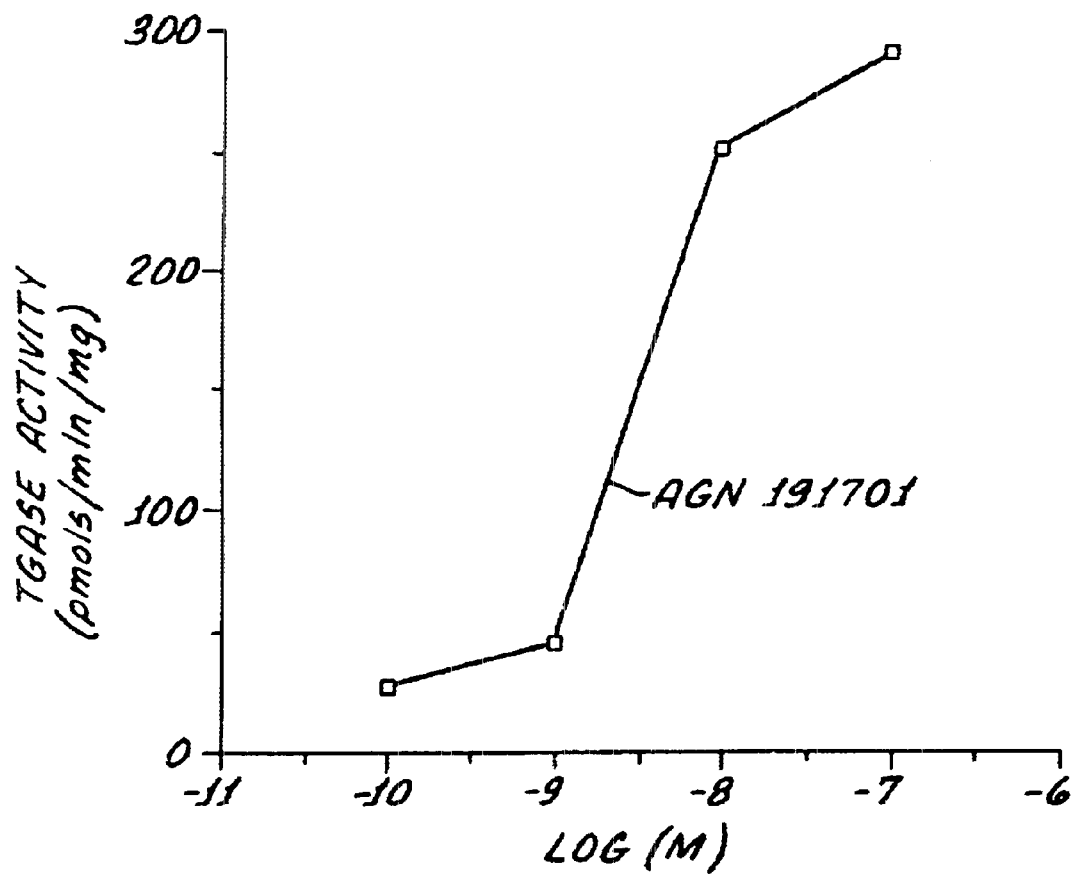
FIGS. 8 is a graph showing the results of the HL 60 Cell transglutaminase assay for AGN 191701 (Compound 19).
Figure 8B:
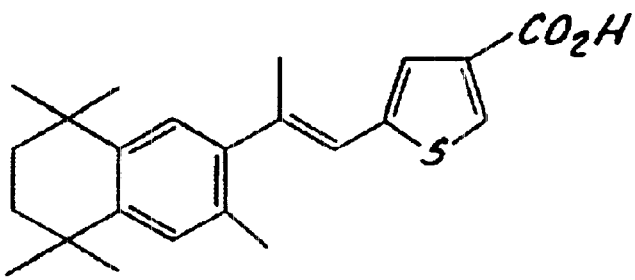
Figure 9A:
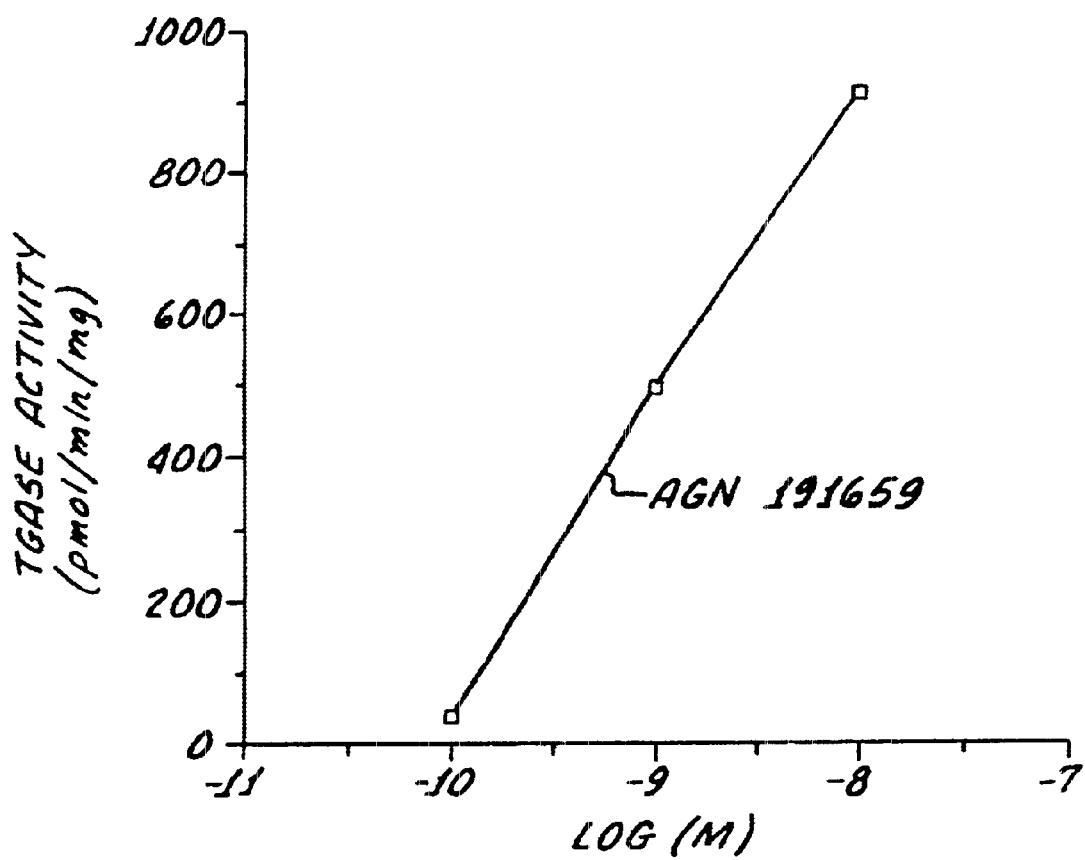
FIGS. 9 is a graph showing the results of the HL 60 Cell transglutaminase assay for AGN 191659 (Compound 21).
Figure 9B:
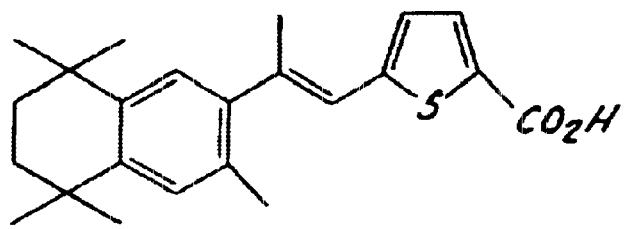

As is well understood in the art, induction of tranglutaminase activity in the just-described assay is an early marker of retinoid like activity. The graph of FIG. 6 shows the results of this test for prior art compound AGN 191183 (Formula 7), and also for AGN 191440 (Compound 11). It can be seen in the graph that in this particular assay the prior art compound is inactive, and AGN 191440 is active. The graphs of FIGS. 7 through 9 show that other exemplary compounds of this invention (AGN 191642 (Compound 13), AGN 191701 (Compound 19), and AGN 191659 (Compound 21)) are also active in this assay.

Another advantageous property of the compounds used in accordance with the methods of treatment of the present invention (and of the novel compounds of the invention) is that the compounds show significantly less toxicity and cause significantly less skin irritation than comparable compounds lacking the structural features in accordance with the present invention. The lessened toxicity of the compounds used in accordance with the methods of treatment of the present invention (and of the novel compounds of the invention as well) is very significant, because toxicity, and specifically irritation of skin is considered a general disadvantage of retinoid like compounds. Therefore, the fact that the structure shown in Formula 1 imparts significantly lessened toxicity and skin irritating effect to the compounds in accordance with the present invention, is surprising and remarkable.

Specifically, tests to determine skin toxicity were performed on certain examplary compounds in accordance with the present invention, and on certain analogous compounds which lack the $R_3$ substituent in accordance with Formula 1, 2 or 3. A "Two Week Acute Skin Toxicity Study of Multiple Topical Applications in Female Hairless Mice" is conducted as follows: a daily dose (expressed in nanomoles) of the "test compound" is applied to the skin on the back of hairless mice (usually a test group of 5 mice for a given compound). The daily dose of the test compound is applied for 5 consecutive days, followed by two days when the test compound is not administered, and is thereafter administered again for 4 more consecutive days. On the 14th day the test animals if still alive, are sacrificed to perform certain studies and tests. In the meanwhile certain tests and observations are made on a daily basis with respect to body weight and skin condition. Skin condition is graded as "flaking/scaling" and "abrasion" on a scale of 0 to +5 where the various numbers correspond to the following observations.

| Primary Skin Irritation Scoring Scale | |
|---|---|
| | Grade |
| Flaking/scaling | |
| No flaking | 0 |
| very slight (few flakes) | +1 |
| Slight (~25% or less) | +2 |
| Mild (greater than ~25%, less than ~50%) | +3 |
| Moderate (greater than ~50%, less than ~75%) | +4 |
| Severe (~75% or more) | +5 |
| Abrasion | |
| No abrasion | 0 |
| Very slight (One to two abrasions with a slight pink color) | +1 |
| Slight (One or more abrasions, dark pink color) | +2 |
| Mild (greater than ~25%, light red color) | +3 |
| Moderate (greater than ~50%, red color) | +4 |
| Severe (greater than ~75%, deep red color) | +5 |

Results of these tests are summarized in Table 3, where daily dose is expressed in nanomoles, weight loss of the test animals is in percentages at the end of the 14 day test period, or at the time the test animal expired, and mortality is expressed with the number of animals which died from a group of 5.

TABLE 3

| Compound | Daily Dose | % Weight Change | Death/ Total | Flaking/ scaling | Abrasion |
|---|---|---|---|---|---|
| AGN191183 | 7.5 | −2.3 | 0/5 | +2 | +1 |
| " | 25 | −13.4 | 0/5 | +4 | +1 |
| " | 75 | −29.8 | 5/5 | +1 | +1 |
| " | 80 | −2.3 | 5/5 | +1 | +2 |
| AGN191440 | 75 | 3.1 | 0/5 | +2 | +1 |
| " | 124 | −2.7 | 0/5 | +2 | +1 |
| " | 1240 | −19.5 | 3/5 | +4 | +2 |
| AGN191548 | 300 | N/A | 2/5 | +5 | +2 |
| AGN191549 | 300 | 3.6 | 0/5 | +1 | 0 |
| AGN191543 | 800 | N/A | 2/5 | +3 | +1 |
| AGN191544 | 800 | 3.6 | 0/5 | +1 | 0 |
| AGN190316 | 55 | −2.0 | 0/5 | +3 | +2 |
| " | 60 | −28.9 | 3/5 | +2 | +3 |
| AGN191422 | 60 | 0.64 | 0/5 | +1 | +2 |
| " | 64 | 1.5 | 0/5 | +1 | +1 |

AGN 191183 is the prior art compound of Formula 7; AGN 191440 is Compound 11 which is structurally identical in every respect with AGN 191183 except that it has the methyl group in the 3-position of the tetrahydronaphthalene nucleus, and is therefore within the scope of the present invention. AGN 191549 is Compound 24. AGN 191548 is a compound which is structurally identical in every respect with AGN 191549 except that it lacks the methyl group in the 7-position of the chroman nucleus, and is therefore not within the scope of the present invention. AGN 191544 is Compound 26. AGN 191543 is structurally identical in every respect with AGN 191544 except that it lacks the methyl group in the benzene ring ortho to the double bond, and is therefore not within the scope of the present invention. AGN 191422 is Compound 10. AGN 190316 is structurally identical in every respect with AGN 191422 except that it lacks the methyl group in the 3-position of the tetrahydronaphthalene nucleus, and is therefore not within the scope of the present invention. The data of Table 3 demonstrate that the compounds in accordance with the present invention cause significantly less death and less skin irritation than the compounds of analogous structures which nevertheless lack the features of the invention.

Preferred Embodiments

Referring now to the generalized structural Formulas 2–6 and with reference to the symbol A in these structures, depicting in effect a side chain on a phenyl group or heterocyclic group (represented respectively by Y, $Y_1$ or $Y_2$), compounds are preferred in the method of treatment of the invention, and also among the novel compounds of the invention, where A is $(CH_2)_n$. Still more preferred are compounds where n is zero.

With respect to the symbol B in Formulas 2–6, compounds are preferred in accordance with the invention where B is —COOH, or an alkali metal salt or organic amine salt thereof. Alternatively, compounds are preferred where B is represented by $COOR_8$ (ester where $R_8$ is lower alkyl), $CONR_9R_{10}$ (amide) —$CH_2OH$ (alcohol), $CH_2OCOR_{11}$, $CH_2OR_{11}$ ($R_{11}$ is lower alkyl; lower alkyl esters and ethers formed with a lower alkanol) or B is —CHO or $CH(OR_{12})_2$, $CHOR_{13}O$ (acetal derivatives), where $R_{12}$ and $R_{13}$ are defined as in connection with Formula 2.

With respect to the symbol Y in Formulas 2 and 3, compounds are preferred in accordance with the methods of treatment of the present invention where Y is phenyl, pyridyl, thienyl or furyl. With respect to Formula 4, depicting novel compounds in accordance with the invention, the preference is for Y1 being thienyl. In Formula 5 and 6 which also depict novel compounds in accordance with the invention, the preference is for compounds where $Y_2$ is phenyl, thienyl or pyridyl.

With respect to the symbol $R_2$ in Formulas 2–6, $R_2$ is preferably hydrogen or lower alkyl, more preferably hydrogen.

As it was noted above, the substituent $R_1$ cannot be hydrogen in accordance with the present invention. $R_1$ is preferably lower alkyl, and most preferably methyl throughout the structures shown in Formulas 2–6. Similarly, $R_3$ cannot be hydrogen in accordance with the invention. This substituent is preferably lower alkyl or halogen, and most preferably methyl, chloro or bromo.

In Formulas 2–5 the $R_5$ and $R_6$ substituents (as applicable) are preferably hydrogen or lower alkyl, more preferably hydrogen, or $R_5$ and $R_6$ are absent.

With respect to the symbol $X_1$ in Formula 2, compounds are preferred in the method of treatment of the present invention where $X_1$ is $CR_5$, and most preferred where $X_1$ is CH. In Formula 3 $X_3$ is preferably sulfur.

With regard to the symbol Z in Formula 2 and 3, and more particularly in Formula 2, Z preferably represents a hydrogen and a lower alkyl group, or two lower alkyl groups, a hydrogen and a lower alkoxy group or two lower alkoxy groups, a hydrogen and a lower thialkoxy group or two lower thioalkoxy groups, or a hydrogen and a lower thioalkeneoxy group having one double bond. Alternatively, Z preferably represents —$(CR_{14})_4$—, —$C(R_{14})_2$—$C(R_{14})_2$—$C(R_{14})_2$—$C(R_{14})_2$—, or —$C(R_{14})_2$—$C(R_{14})_2$—$C(R_{14})_2$—$X_2$—. Among these compounds those are preferred where $R_{14}$ is hydrogen or lower alkyl, most preferably methyl, and $X_2$ is preferably O, or S. Still more preferred, in connection with the symbol Z in Formula 2 are the compounds where Z represents one of the following: $C(CH_3)_2$—$CH_2$—$CH_2$—$C(CH_3)_2$— (3,5,5,8,8,-pentamethyl-tetrahydronaphthalene derivatives); $C(CH_3)_2$—$CH_2$—$CH_2$—O— (4,4,7-trimethyl-2,3-dihydrochroman derivatives); $C(CH_3)_2$—$CH_2$—$CH_2$—S— (4,4,7-trimethyl-2,3-dihydrothiochroman derivatives); $C(CH_3)_2$—$CH_2$—$C(CH_3)_2$—O— (2,2,4,4,7-pentamethyl-2,3-dihydrochroman derivatives), and $C(CH_3)_2$—$CH_2$—$C(CH_3)_2$—S— (2,2,4,4,7-pentamethyl-2,3-dihydrothiochroman derivatives).

With regard to Formula 4 and 5, the symbols $R_{20}$ preferably represent lower alkyl groups, and most preferably methyl groups. With respect to Formula 6 one of $R_{21}$ and $R_{22}$ is preferably branch chained lower alkyl group, most preferably a t-butyl group.

The most preferred compounds used as substantially non-teratogenic and non-irritating retinoid like therapeutic agents in the method of treatment of the present invention are, with reference to Formula 8, 9, 10 and 11, are as follows.

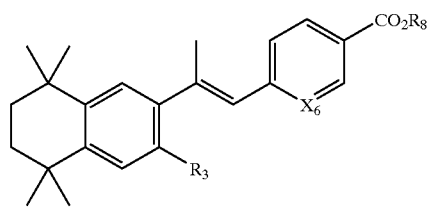

Formula 8

With reference to Formula 8:

| Compound # | $R_3$ | $X_6$ | $R_8$ |
|---|---|---|---|
| 10 | $CH_3$ | CH | Et |
| 11 | $CH_3$ | CH | H |
| 12 | Cl | CH | Et |
| 13 | Cl | CH | H |
| 14 | Br | CH | Et |
| 15 | Br | CH | H |
| 16 | $CH_3$ | N | Et |
| 17 | $CH_3$ | N | H |

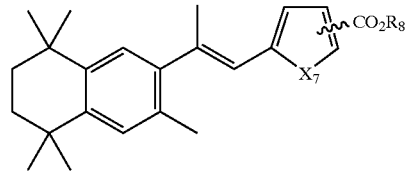

Formula 9

With reference to Formula 9:

| Compound # | $X_7$ | $R_8$ |
|---|---|---|
| 18 | S | Et ($COOR_8$ in position 4) |
| 19 | S | H ($COOR_8$ in position 4) |
| 20 | S | Et ($COOR_8$ in position 5) |
| 21 | S | H ($COOR_8$ in position 5) |
| 22 | O | Et ($COOR_8$ in position 5) |
| 23 | O | H ($COOR_8$ in position 5) |

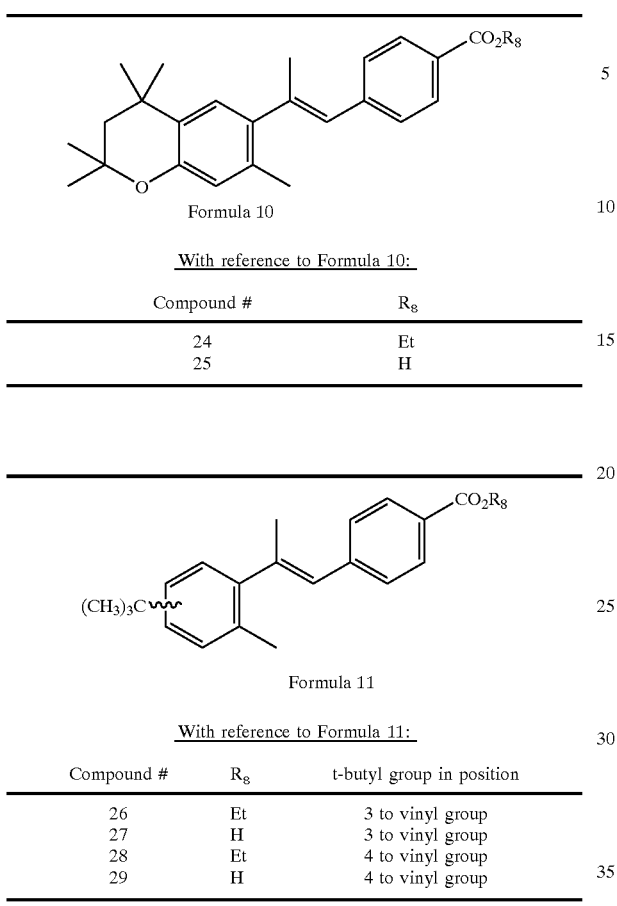

Formula 10

With reference to Formula 10:

| Compound # | $R_8$ |
|---|---|
| 24 | Et |
| 25 | H |

Formula 11

With reference to Formula 11:

| Compound # | $R_8$ | t-butyl group in position |
|---|---|---|
| 26 | Et | 3 to vinyl group |
| 27 | H | 3 to vinyl group |
| 28 | Et | 4 to vinyl group |
| 29 | H | 4 to vinyl group |

Synthetic Procedures for Obtaining the Compounds in Accordance with the Invention The novel compounds of the invention as well as the compounds which are used in accordance with the novel method of treatment of the present invention can be made by a number of different synthetic chemical pathways. To illustrate the invention the following synthetic schemes are provided. The synthetic chemist will readily appreciate that the conditions set out here are specific embodiments for making novel compounds of the invention which can be generalized to any and all novel compounds described in the present specification, and further that the conditions can be generalized to obtain any and all compounds which are to be used as non-teratogenic pharmaceutically active agents in the methods of treatment of the present invention.

REACTION SCHEME 1

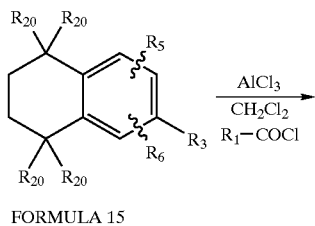

FORMULA 15

FORMULA 16

FORMULA 17

FORMULA 18

↓

HOMOLOGS AND DERIVATIVES

Referring to Reaction Scheme 1, the synthesis of the phenyl-propenyl 5,6,7,8-tetrahydronaphthalene compounds utilized in the method of the present invention is illustrated. In accordance with Reaction Scheme 1, a 5,5,7,8-tetrahydronaphthyl compound which has the desired $R_3$, $R_5$, $R_6$ and $R_{20}$ substituents (as these are defined in connection with Formula 4) is reacted under Friedel Crafts-like conditions with a reagent such as $R_1COCl$ ($R_1$ is defined as in connection with Formula 4) to introduce the $R_1$—CO— ketone function into the 2-position of the naphthalene nucleus. When $R_1$ is methyl, then the reagent in the Friedel Crafts type reaction is typically acetyl chloride. The resulting ketone of Formula 16 is then subjected to a Wittig Horner type reaction with a phosphonate reagent of Formula 17. The phosphonate reagent of Formula 17 carries an ester ($COOR_8$) substituent, but it should be understood that an analogous phosphonate reagent can, generally speaking, carry the A—B functionality, as such functionality is defined in connection with Formula 2. The Wittig Horner type reaction is conducted in the presence of strong base, such as $NaCH_2SOCH_3$ (dimsyl sodium) in a solvent like tetrahydrofuran (THF), as is indicated in the reaction scheme. The ethylenic bond (double bond) of the compounds of Formula 18 is formed in this reaction. As is stated above, this double bond is a required feature of the compounds used in accordance with the present invention.

The compounds of Formula 18 may be subjected to further transformations, particularly as far as synthetic transformation of the $COOR_8$ group is concerned. As far as the synthesis of compounds analogous to the compounds of Formula 18, but differring therefrom in the functionality of the A–B group (see for example Formula 2) is concerned, (and by extension of the principles to any and all compounds used in accordance with the invention) the following further well known and published general principles and synthetic methodology are noted.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide and dimethylaminopyridine. The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

To increase the value of n before affecting the Wittig Horner (or analogous) coupling reaction of Reaction Scheme 1 (where such compounds corresponding to Formula 17 are not available from a commercial source) aromatic or heteroaromatic carboxylic acids are subjected to homologation by successive treatment under Arndt-Eistert conditions or other homologation procedures. Alternatively, derivatives which are not carboxylic acids may also be homologated by appropriate procedures. The homologated acids can then be esterified by the general procedure outlined in the preceding paragraph.

An alternative means for making compounds where A is $(CH_2)_n$ (n is 1–5) is to subject the compounds of Formula 2, (or of Formula 18) where B is an acid or other function, to homologation, using the Arndt-Eistert method referred to above, or other homologation procedures.

Compounds of Formula 2, where A is an alkenyl group having one or more double bonds can be made for example, by having the requisite number of double bonds incorporated into the intermediate which is coupled as a phosphonate with the ketone of Formula 16. Generally speaking, such compounds where A is an unsaturated carbon chain can be obtained by synthetic schemes well known to the practicing organic chemist; for example by Wittig and like reactions, or by introduction of a double bond by elimination of halogen from an alpha-halo-arylalkyl-carboxylic acid, ester or like carboxaldehyde. Compounds of Formula 2 where the A group has a triple (acetylenic) bond can be made by using the corresponding phosphonate intermediate. Such intermediate can be obtained by reactions well known in the art, for example, by reaction of a corresponding aromatic-methyl ketone with strong base, such as lithium diisopropyl amide.

The acids and salts derived from compounds of Formula 2 and of Formula 18 are readily obtainable from the corresponding esters. Basic saponification with an alkali metal base will provide the acid. For example, an ester of Formula 2 or of Formula 18 may be dissolved in a polar solvent such as an alkanol, preferably under an inert atmosphere at room temperature, with about a three molar excess of base, for example, potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the acid is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 0 degrees C and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alky halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethlaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K., Swern, D., *Tetrahedron*,1978,34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Compounds of Formula 2 where B is H can be prepared from the corresponding halogenated aromatic compounds, preferably where the halogen is I.

Reaction Scheme 2

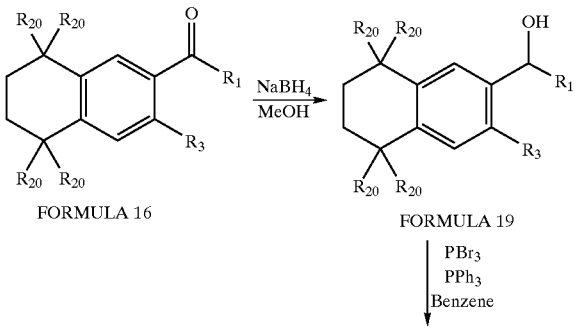

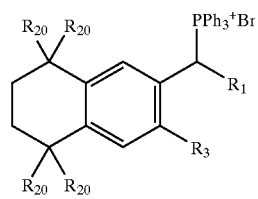

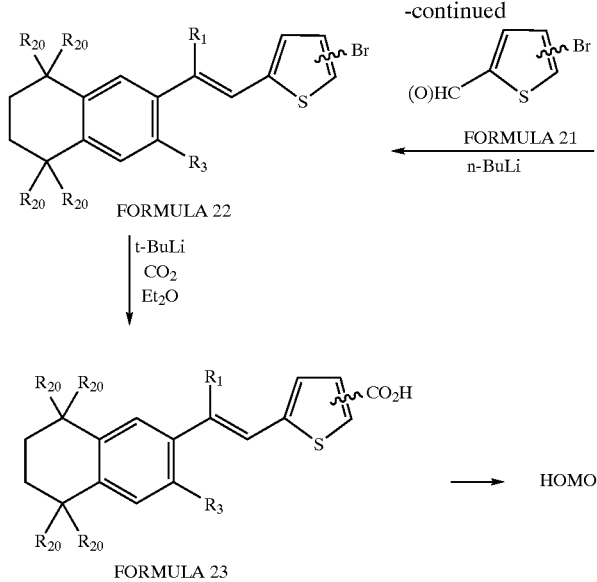

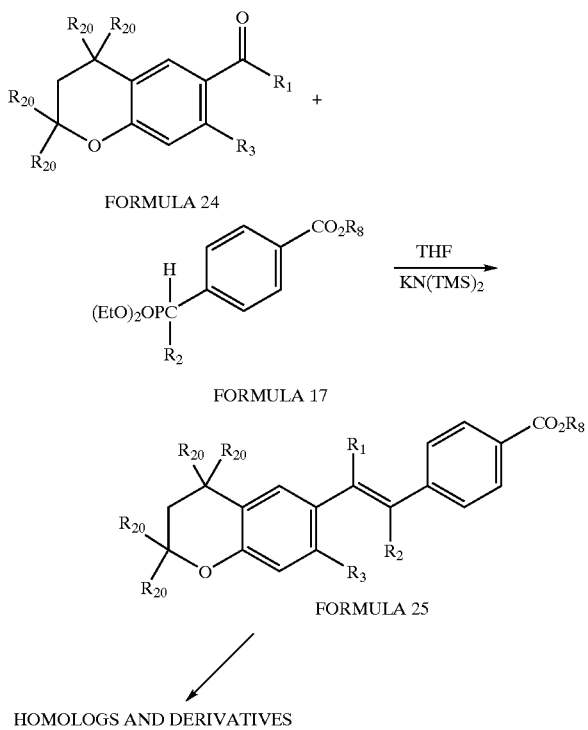

Reaction Scheme 2 illustrates another example of a synthetic procedure for preparing the compounds used in accordance with the invention, specifically as applied for the synthesis of compounds where the Y group in Formula 2 is heteroaryl, such as thienyl. Thus, in accordance with this examplary reaction scheme, the ketone of Formula 16 is reduced (for example with sodium borohydride) to the corresponding alcohol of Formula 19. The alcohol of Formula 19 is converted to the corresponding phosphonium salt (for example triphenyl phosphonium bromide) by treatment with the appropriate reagents, such as phosphorous tribromide and triphenylphosphine. The phosphonium salt of Formula 20 is a Wittig reagent, which is reacted with a bromo thiophene aldehyde of Formula 21, under Wittig conditions (base such as n-butyl lithium). The compound of Formula 22 which is formed as a result of the latter reaction has the essential structural features of the compounds used in accordance with the present invention, namely the $R_1$ substituent on the double bond, and the $R_3$ substituent on the adjacent aromatic ring carbon, as well the aromatic or heteroaromatic group as yet another substituent on the double bond. The bromo group of the thiophene moiety of the compound of Formula 22 is converted into a carboxyl group by reaction with t-butyl lithium and capture of carbon dioxide. The compounds of Formula 23 are active agents in accordance with the present invention, and can also be converted into further homologs and derivatives, as described above.

An example of a variation of the procedure outlined in Reaction Scheme 2 is a reaction between the triphenylphosphonium salt of Formula 20 and 4-carbethoxybenzaldehyde by heating in 1,2-epoxybutane. This reaction is particularly advantageously conducted when $R_3$ of Formula 16 is chloro. The products of these Wittig-type reactions are compounds which are used in accordance with the methods of treatment of the invention; when $R_{20}$ is methyl and $R_3$ is Cl, then the product is Compound 12.

Reaction Scheme 3 provides another example of preparing compounds in accordance with the present invention by utilizing a Wittig Horner type reaction between a chroman derivative ketone of the Formula 24 and a phosphonate of the Formula 17. ($R_1$, $R_3$, and $R_{20}$ in Formula 24 are defined the same as in connection with Formula 4.) The chroman derivative of Formula 24 can be obtained in accordance with the teachings of U.S. Pat. No. 4,980,369, and specifically as is described with reference to Reaction Scheme 2 in that patent, and in analogy to the actual example provided in that reference patent for preparing 2,2,4,4,7-pentamethyl-6-acetylchroman (Column 20 line 58). The specification of U.S. Pat. No. 4,980,369 is expressly incorporated herein by reference. Thus, the chroman derivative of Formula 24 is coupled in the presence of potassium bis(trimethylsilyl) amide in tetrahydrofuran with the phosphonate of Formula 17 to yield the compounds of Formula 25 which are active agents in accordance with the present invention. An example of a preferred compound in accordance with Formula 25 is Compound 24. The compounds of Formula 25 can also be derivatized or converted into homologs, as described above. For example, Compound 25 is obtained by saponification of Compound 24.

Reaction Scheme 4

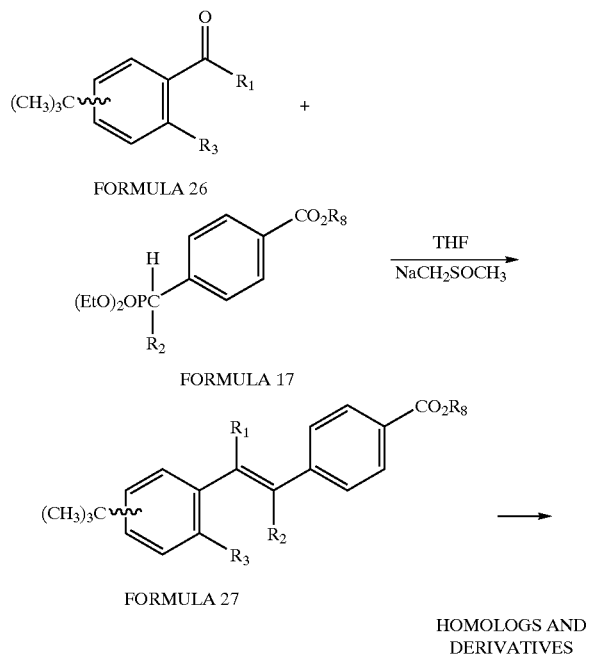

FORMULA 26

FORMULA 17

FORMULA 27

HOMOLOGS AND DERIVATIVES

Reaction Scheme 4 illustrates another example of a synthetic route for obtaining the compounds of the present invention, particularly where with reference to Formula 2 the symbol Z represents one or two lower alkyl groups and $X_1$ represents CH, and specifically when Z represents a t-butyl group.

In accordance with Reaction Scheme 4, the substituted acetophenone ($R_1=CH_3$), or acetophenone homolog of Formula 26 is reacted in a Wittig Horner type reaction (such as in the presence of dimsyl sodium in tetrahydrofuran) with the phosphonate of Formula 17. The compounds of Formula 27 obtained in this manner are active agents in accordance with the invention. The compounds of Formula 27 can also be derivatized and converted into homologs, as described above. Examples of preferred compounds which are obtained in accordance with this reaction scheme are Compounds 26–29.

The foregoing synthetic routes together with the specific examples which are provided below are believed to enable the practicing organic chemist to obtain any and all compounds which are active agents in accordance with the methods of treatment of the present invention. Nevertheless, by way of further illustration and examples, the following is noted. Generally speaking, the compounds of the invention can be obtained in accordance with the reactions set forth in Reaction Schemes 5–8.

Reaction Scheme 5

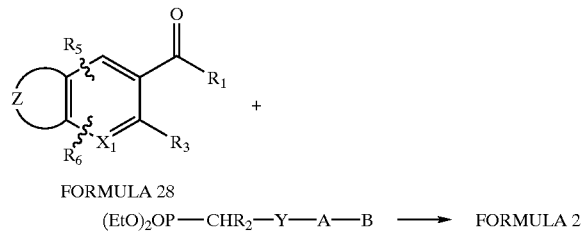

FORMULA 28

(EtO)$_2$OPCHR$_2$—Y—A—B   ⟶   FORMULA 2

FORMULA 29

Reaction Scheme 6

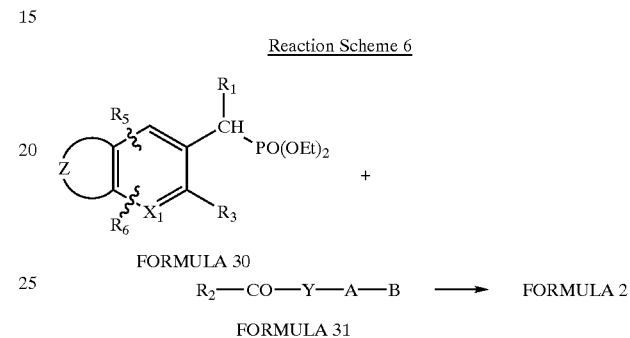

FORMULA 30

R$_2$CO—Y—A—B   ⟶   FORMULA 2

FORMULA 31

Reaction Scheme 7

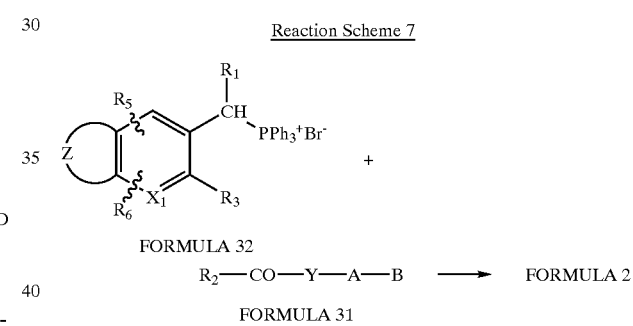

FORMULA 32

R$_2$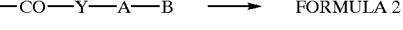CO—Y—A—B   ⟶   FORMULA 2

FORMULA 31

Reaction Scheme 8

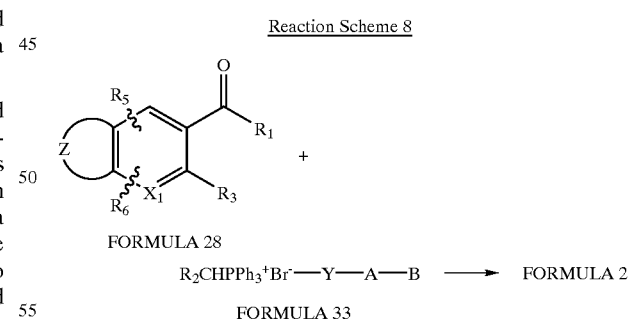

FORMULA 28

R$_2$CHPPh$_3^+$Br$^-$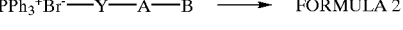—Y—A—B   ⟶   FORMULA 2

FORMULA 33

The reaction shown in Reaction Scheme 5 is generally known in the art as a Wittig Horner reaction, sometimes this reaction is also referred to as the Horner Emmons reaction. It involves the reaction of a ketone with a phosphonate under basic conditions to form an olefinic bond, in accordance with the scheme, to provide the compounds of Formula 2. The reactants in this reaction scheme are the aromatic or heteroaromatic ketone of Formula 28 and the aromatic or heteroaromatic phosphonate of Formula 29. The symbols in these formulas are defined as in connection with Formula 2. The heteroaromatic ketones of Formula 28 can, generally speaking, be obtained by procedures well known and published in the chemical literature; frequently such procedures involve the introduction of the $R_1CO$ group, (the $CH_3CO$ group when $R_1=CH_3$) by a Friedel-Crafts or like reaction to the otherwise appropriately substituted aromatic or heteroaromatic compound. Actual examples for preparing phosphonates corresponding to Formula 29 are provided below. Generally speaking, such phosphonates can be obtained by reacting the alkylated aromatic or heteroaromatic compound having the structure $R_2$—$CH_2Y$—A—B with N-bromosuccinimide, and thereafter reacting the resulting bromo compound $R_2$—CHBrY—A—B with triethylphosphite. Generally speaking, the Wittig Horner reaction illustrated in Reaction scheme 5 is the preferred procedure for preparing the compounds of Formula 2 and of Formula 3 as well when the A—B functionality represents a reasonably strong electron withdrawing group (such as an ester).

Reaction Scheme 6 illustrates an alternative route for utilizing the Wittig Horner reaction for preparing the compounds of Formula 2 and by analogy of Formula 3 as well. The symbols have the same definitions as in connection with Formula 2. In this reaction scheme, the phosphonate of Formula 30 is formed from the aromatic or heteroaromatic moiety which is analogous to the compounds of Formula 28. The phosphonates of Formula 30 can be derived, generally speaking, from the ketones of Formula 28 through reduction, and conversion of the resulting alcohol into a halide (preferably bromide) and thereafter into the phosphonate. The aromatic or heteroaromatic aldehydes or ketones of Formula 31 can be obtained by procedures readily available to the practicing organic chemist.

Reaction Scheme 7 illustrates another preferred general procedure for obtaining the compounds of Formula 2, and by analogy of Formula 3 as well. The symbols in this reaction scheme are defined as in connection with Formula 2. In accordance with this procedure, a phosphonium salt, preferably a triphenylphosphonium salt of Formula 32, is obtained for example from the ketone of Formula 28. The phosphonium salt of Formula 32 can be obtained from the ketone compounds of Formula 28 by reduction to an alcohol, and subsequent reaction with phosphorous tribromide and triphenylphosphine, in analogy to the reaction described in connection with Reaction Scheme 2. The phosphonium salt of Formula 32 is thereafter reacted with the aromatic or heteroaromatic aldehyde or ketone of Formula 31 in a Wittig reaction, involving the action of strong base, such as n-butyl lithium.

Reaction Scheme 8 illustrates an alternative Wittig reaction as a general procedure for obtaining the compounds of Formula 2, and by analogy of Formula 3 as well. The symbols in this reaction scheme are defined as in connection with Formula 2. In accordance with this procedure the aromatic or heteroaromatic ketone of Formula 28 is reacted, in the presence of strong base with a phosphonium salt, preferably with a triphenylphosphonium bromide of Formula 33. The triphenylphosphonium bromide of Formula 33 can be obtained, for example, by reaction of the bromo compound $R_2$—CHBrY—A—B with triphenylphosphine.

Examples of reagents in accordance with Formulas 29, 31 and 33 to be used in the Wittig Horner or Wittig and analogous coupling reactions to provide the compounds used in the methods of treatment of the present invention, are as follows:

ethyl [4-(diethoxyphosphinyl)methyl]benzoate (Compound 40);
Diethyl (3-carboethoxybenzyl)phosphonate;
Diethyl (2-carboethoxybenzyl)phosphonate;
Diethyl (2-carboethoxy-5-thiophenyl)methylphosphonate (Compound 41)
Ethyl 2-[5-(diethoxyphosphinyl)methyl]furancarboxylate (Compound 42);
Ethyl-3-[5-[(diethoxyphosphinyl)methyl]]nicotinoate (Compound 43)

Examples of reagents in accordance with Formula 28, 30 and 32 to be used in the Wittig Horner or Wittig and analogous coupling reactions to provide the compounds used in the methods of treatment of the present invention, are as follows:

Methyl [3,5,5,8,8-pentamethyl(5,6,7,8-tetrahydronaphthalen)-2-yl]ketone (Compound 50)
1-(3,5,5,8,8-pentamethyl-5,6,7,8-tetrahydronaphthalen-2-yl)-ethan-1-yl-triphenylphosphonium bromide (Compound 51);
2,2,4,4,7-pentamethyl-6-acetylchroman (Compound 52) see U.S. Pat. No. 4.980,369;
2-methyl-5-t-butylacetophenone (Compound 53); obtainable in accordance with the chemical literature, *J. Amer. Chem. Soc.*, 77, p 1696 (1955); *Chem. Ber.*, 32, p 2422 (1899); *J. Org. Chem.*, 22, pp 25–29 (1957);
Methyl [3-chloro-5,5,8,8-tetramethyl(5,6,7,8-tetrahydronaphthalen)-2-yl]ketone (Compound 54);
[(5,6,7,8-tetrahydro-3-chloro-5,5,8,8-tetramethylnaphthalen-2-yl)ethan-1-yl] triphenylphosphonium bromide (Compound 55);
2-methyl-4-t-butylacetophenone (Compound 56); obtainable in accordance with the chemical literature, *Chem. Ber.*, 31, p. 1345 (1898); *J. Org. Chem.*, 22, pp 25,26 (1957); *J. Chem. Soc.*, 1952, p. 1123;
Methyl [3-bromo-5,5,8,8-tetramethyl(5,6,7,8-tetrahydronaphthalen)-2-yl]ketone (Compound 57);
Methyl (3-ethyl-5,5,8,8-tetramethyl-(5,6,7,8-tetrahydronaphthalen)-2-yl]ketone (Compound 58);
Methyl 3-isopropyl [5,5,8,8-tetramethyl(5,6,7,8-tetrahydronaphthalen)-2-yl]ketone (Compound 59);
Ethanone, 1-(5,6,7,8-tetrahydro-2-methyl-3-quinolinyl), obtainable in accordance with the chemical literature, CA79(13):78555k; Chem. Ber. 106(6), 1736–42 (1973);
Ethanone, 1-(2-methyl-3-quinolinyl), obtainable in accordance with the chemical literature, CA90(19):152027k German Offenlegungsschrift DE 2730061 Jan. 18, 1979;
Ethanone, 1-(3-methyl-2-naphthalenyl), obtainable in accordance with the chemical literature, CA111(19):173803c, Japanese Patent JP 01047734 A2, Feb. 22, 1989;
Ethanone, 1-(2-methyl-1H-inden-3-yl), obtainable in accordance with the chemical literature, CA95(23):202928f, J. Org. Chem. 46(24), 5022–5 (1981);
Ethanone, 1-(2-methyl-1H-indol-3-yl), obtainable in accordance with the chemical literature, CA115(15):159291k, Tetrahedron 47(28) 5111–18 (1991);
Ethanone, 1-(2-methylbenzo[b]thien-3-yl), obtainable in accordance with the chemical literature, CA85(25):192542c, French Patent Application FR 2279395 Feb. 20, 1976;
Ketone, methyl 4,5,6,7-tetrahydro-2-methylbenzo[b]thien-3-yl, obtainable in accordance with the chemical literature, Bull. Soc. Chim. France 3, 359–361 (1958);
Ethanone, 1-(4,5,6,7-tetrahydro-2-methyl-3-benzofuranyl), obtainable in accordance with the chemical literature, CA91(18):148446z, J. Org. Chem. 44(20) 3519–23 (1979);

Ethanone, 1-(4,5,6,7-tetrahydro-2-methyl-1H-indol-3-yl, obtainable in accordance with the chemical literature, CA82(17):111890c, Ann. Chim. (Rome) 63(9–10) 601–6 (1973);

Thieno[2,3-b]pyridine, 7-acetyl-4,5,6,7-tetrahydro-2-methyl, obtainable in accordance with the chemical literature, CA110(15):135007t, Tetrahedron 44(15) 4777–86 (1988);

Ethanone, 1-[6-(methoxymethyl)-5-benzofuranyl], obtainable in accordance with the chemical literature, CA87(l):5839m, J. Chem. Soc., Perkin Trans. 1(4), 423 (1977);

Ethanone, 1-(6-chloro-3-methyl-5-benzofuranyl), obtainable in accordance with the chemical literature, CA78 (17):110781y, Indian J. Chem. 10(11) 1065–7 (1972).

Further examples of reagents in accordance with Formula 26 to be used in the Wittig Horner or Wittig and analogous coupling reactions to provide the compounds used in the methods of treatment of the present invention, can be obtained in accordance with well known and established procedures, for example by acylation (acetylation) under Fridel-Crafts like conditions of further known aromatic and heteroaromatic compounds, such as 6-methyl-benzofuran (CA103(9):71182s); 6-methyl-1H-indole (CA114(23):228730w) and 6-methylbenzo[b]thiophene (CA114(15):143128f).

SPECIFIC EXAMPLES

4-Carboethoxy-benzylbromide

To a stirred solution of 16.09 g (78 mmol) of 1,3-dicyclohexylcarbodiimide (Aldrich) in 100 ml methylene chloride was added a suspension of 15.4 g (71 mmol) of 4-carboxybenzylbromide in 100 ml methylene chloride and then 4.9 g (106.5 mmol) of absolute ethanol and 0.81 g (7.1 mmol) of 4-dimethylaminopyridine. A further 50 ml of methylene chloride was added to the reaction mixture and mixture heated at reflux for 2 hours. The mixture was allowed to cool to room temperature and the resultant white precipitate removed by filtration. The filtrate was washed with water, dried (MgSO$_4$) and then concentrated in-vacuo to give the title compound as a colorless oil which crystallized on standing. PMR (CDCl$_3$); δ 1.39 (3H, t, J=7.2 Hz), 4.38 (2H, q, J=7.2 Hz), 4.50 (2H, s), 7.45 (2H, d, J=7.7 Hz), 8.03 (2H, d, J=7.7 Hz).

Ethyl [4-(Diethoxyphosphinyl)methyl]benzoate (Compound 40)

A mixture of 11.8 g (48 mmol) of 4-carboethoxybenzylbromide and 12.0 g (72 mmol) of freshly distilled triethylphosphite was placed in a flask fitted with an argon inlet and a dry-ice cooled trap. A continuous stream of argon was passed over the stirred reaction mixture and mixture heated at 120° C. for 3 hours at which time no further ethyl bromide was being formed. The residue was purified by vacuum distillation to give the title compound as a colorless oil, BP=170°/0.35 mm). PMR (CDCl$_3$): δ 1.23 (6H, t, J=7.1 Hz), 1.39 (3H, t, J=6.9 Hz), 3.21 (2H, d, J=22.1 Hz), 4.02 (4H, m), 4.37 (2H, q, J=7.5 Hz), 7.38 (2H, d, J=7.9 Hz), 8.00 (2H, d, J=7.9 Hz).

Ethyl 5-Methyl-2-thiophenecarboxylate

To a stirred solution of 15.9 g (77.4 mmol) of 1,3-dicyclohexylcarbodiimide in 40 mL dichloromethane was added 10 g (70.3 mmol) of 5-methyl-2-thiophenecaboxylic acid and 4.85 g (105.5 mmol) of anhydrous ethanol. 0.86 g of dimethylaminopyridine was then added and the suspension stirred at room temperature for 20 hours. The resulting white precipitate was removed by filtration. The filtrate was washed with water, dried (MgSO$_4$), filtered and concentrated under reduced pressure. The residue was purified by bulb-to-bulb distillation (bp=95° C., 3 mm Hg) to give the title compound as a clear, pale yellow oil.

PMR (CDCl$_3$): δ 1.36 (3H, t, J=7.1 Hz), 2.52 (3H, s), 4.32 (2H, q, J=7.1 Hz), 6.76 (1H, d, J=3.8 Hz), 7.61 (1H, d, J=3.8 Hz).

Ethyl 5-Bromomethyl-2-thiophenecarboxylate

N-Bromosuccinimide (23.5 g, 132 mmol), benzoyl peroxide (0.26 g) and 90 mL of benzene were brought to reflux under argon. Ethyl 5-methyl-2-thiophenecarboxylate (22.5 g, 132 mmol) was added dropwise through an addition funnel and the resulting mixture was refluxed for 6 hours and then cooled to room temperature and stirred for 16 hours. The mixture was treated with 50 mL of water and extracted with 3 X 75 mL ether.

The ether extracts were combined and washed with 75 mL saturated aqueous NaCl and then dried (MgSO$_4$). The solvent was removed in-vacuo and the residual oil purified by flash chromatography (SiO$_2$, 99:1, ethyl acetate in hexanes) to give the title compound as a clear, yellow oil.

PMR (CDCl$_3$): δ 1.37 (3H, t, J=7.3 Hz), 4.35 (2H, q, J=7.3 Hz), 4.68 (3H, s), 7.09 (1H, d, J=4.0 Hz), 7.64 (1H, d, J=4.0 Hz).

Ethyl 5-[(Diethoxyphosphinyl)methyl]-2-tiophenecarboxylate (Compound 41)

A mixture of 4.99 g (20.0 mmol) of ethyl 5-bromomethyl-2-thiophenecarboxylate and 5.17 mL (30.0 mmol) of triethylphophite was heated to 120° C. under argon for 6 hours and the excess triethylphosphite removed by distillation.

The product was purified by vacuum distillation (bp=175°, 3 mm Hg) to give the title compound as a clear, pale yellow oil.

PMR (CDCl$_3$): δ 1.30 (6H, t, J=7.1 Hz), 1.37 (3H, t, J=7.2 Hz), 3.38 (2H, d, J=20.9 Hz), 4.05–4.15 (4H, m), 4.33 (2H, q, J=7.1 Hz), 6.99 (1H, dd, J=3.6, 3.6 Hz), 7.66 (1H, d, J=1.1, 3.6 Hz).

Ethyl 2-(5-Bromomethyl)furancarboxylate

To a suspension of 1.32 g (7.4 mmol) of N-bromosuccinimide and 10.9 mg of benzoyl peroxide in 8 mL of carbontetrachloride was added a solution of ethyl-2-(5-methyl)furancarboxylate in 8 mL of carbontetrachloride and the resulting mixture stirred at 55° C. for 8 hours. The mixture was then filtered, concentrated and residual oil purified using flash chromatography (SiO$_2$, 5% ethyl acetate in hexanes) to give the title compound as a clear oil.

Ethyl 2-[5-(Diethoxyphosphinyl)methyl] furancarboxylate (Compound 42)

A solution of 1.84 g (1.30 ml, 14.8 mmol) of triethylphosphite and 0.84 g (3.6 mmol) of ethyl-2-(5-bromomethyl) furancarboxylate was heated at 125° C. under argon for 30 hours. The solution was then cooled and purified using kuegelrohr distillation (165–180° C., 1 mm Hg) to give the title compound as a clear oil.

Ethyl [5-Bromomethyl]nicotinoate

To a solution of ethyl-3-[5-methyl]nicotinoate in 10 mL of carbontetrachloride was added 10.9 mg of benzoyl peroxide and a tipfull of N-bromosuccinimide. The mixture was heated to 60° C. and the remaining 1.19 g (6.7 mmol, total) of N-bromosuccinimide was taken-up in 20 mL of carbontetrachloride and added to the heating mixture. The resulting mixture was stirred ato 60° C. for 3 hours and at room temperature for 12 hours. Additional benzoyl peroxide was then added (9 mg) followed by 4 hours of additional heating. The mixture was then cooled, filtered, concentrated and the residual oil purified using flash chromatography (SiO$_2$, 10% ethyl acetate in hexanes) to give the title compound as a pinkish solid.

Ethyl-3-[5-(Diethoxyphosphinyl)methyl]nicotinoate (Compound 43)

A solution of 0.99 g (0.70 ml, 7.98 mmol) of triethylphosphite and 0.21 g (8.6 mmol) of ethyl-3-[5-bromomethyl] nicotinoate were heated at 130° C. under argon for 24 hours and at room temperature for 48 hours. The solution was then cooled and purified using kuegelrohr distillation (155–165° C., 1 mm Hg) to give the title compound as a yellow oil.

Methyl [3,5,5,8,8-Pentamethyl(5,6,7,8-tetrahydronaphthalen)-2-yl]ketone (Compound 50)

To a suspension of 6.71 g (50.3 mmol) of aluminum chloride in methylene chloride at 0° C. under argon was added a solution of 3.95 g (3.58 mL, 50.3 mmol) of acetyl chloride and 10.21 g (41.9 mmol) of 3,5,5,8,8-pentamethyl-5,6,7,8-tetrahydronaphthalene in methylene chloride. The resulting mixture was allowed to warm to room temperature over a period of 3 hours with stirring. The mixture was recooled to 0° C. and 1N HCl was dropwise added. The mixture was then taken-up in water and extracted three times with methylene chloride. The organic layers were washed with 1N HCl, water, brine, and dried (MgSO$_4$). Solvent was removed in-vacuo and the resulting residue purified using flash chromatography to give the title compound as an ivory solid.

PMR (CDCl$_3$): δ 1.28 (6H, s), 1.30 (6H, s), 1.69 (4H, s), 2.49 (3H, s), 2.57 (3H, s), 7.15 (1H, s), 7.67 (1H, s).

Ethyl 4-[(E)-2-(5,6,7,8-Tetrahydro-3,5,5,8,8-pentamethylnaphthalen-2-yl)propen-1-yl]benzoate (Compound 10)

A solution of 5.0 g (21.5 mmol) of methyl [3,5,5,8,8-pentamethyl(5,6,7,8-tetrahydro-naphthalen)-2-yl]ketone (Compound 50) and 3.39 g (11.3 mmol) of ethyl (4-(diethoxyphosphinyl)methyl]benzoate, (Compound 40) in 25 mL of tetrahydrofuran was added via cannula into a suspension of 0.52 g (21.5 mmol) of sodium hydride in 25 mL of tetrahydrofuran at 0° C. under argon. The resulting suspension was allowed to warm to room temperature and stirred for 16 hours. The resulting sludge was taken-up in water and 1N HCl and extracted with ether. The ether layers were washed with water, brine, and dried (MgSO$_4$). The solvent was removed in-vacuo and the residue purified using flash chromatography (SiO$_2$, 1% ethyl acetate in hexanes) to give a mixture of isomers which were separated using HPLC (0.5% ethyl acetate in hexanes) to give the title compound as a white solid.

PMR (CDCl$_3$): δ 1.30 (12H, s), 1.38 (3H, t, J=7.0 Hz), 1.69 (4H, s), 2.21 (3H, s), 2.30 (3H, s), 4.39 (2H, q, J=7.1 Hz), 6.42 (1H, s), 7.12 (2H, overl. s), 7.43 (2H, d, J=8.3 Hz), 8.05 (2H, d, J=8.3 Hz).

4-(E)-2-(5,6,7,8-Tetrahydro-3,5,5,8,8-pentamethylnaphthalen-2-yl)propen-1-yl]benzoic Acid (Compound 11)

A solution of potassium hydroxide in ethanol was added to 95 mg (0.25 mmol) of ethyl 4-[(E)-2-(5,6,7,8-tetrahydro-3,5,5,8,8-pentamethylnapth)-2-yl)propen-1-yl]benzoate (Compound 10) and the resulting mixture stirred at room temperature. Solvent was removed in-vacuo and the resulting solid taken-up in water, acidified using 1N HCl, and extracted three times with ether. The ether extracts were washed with water, brine and dried (MgSO$_4$). The solvent was removed in-vacuo to give the title compound as an orange solid.

PMR (d$^6$-DMSO): δ 1.23 (12H, s), 1.62 (4H, s), 2.15 (3H, s), 2.23 (3H, s), 6.37 (1H, s), 7.08 (1H, s), 7.13 (1H, s), 7.51 (2H, d, J=8.3 Hz), 7.94 (2H, d, J=8.3 Hz).

2-[(E)-2-(5,6,7,8-Tetrahydro-3,5,5,8,8-pentamethyl-2-naphthalen-2-yl)propen-1-yl]-4-bromothiophene To a solution of 0.56 g (0.98 mmol) of 1-(3,5,5,8,8-pentamethyl-5,6,7,8-tetrahydro-naphthalen-2-yl)ethan-1-yltriphenylphosphonium bromide (Compound 51) in 11 mL of tetrahydrofuran at −78° C. under argon was added dropwise 0.41 g (0.61 mL, 0.98 mmol, 1.6 M in hexanes) of n-BuLi. The resulting suspension was allowed to warm to room temperature and then a solution of 0.28 g (1.47 mmol) of 4-bromo-2-thiophenecarboxaldehyde in 2 mL of tetrahydrofuran was dropwise added and the resulting mixture stirred for 20 hours at room temperature. The solvent was removed in-vacuo and the resulting solid taken-up in water, acidified using 1N HCl, and extracted three times with ether. The ether extracts were washed with water, brine and dried (MgSO$_4$). The solvent was removed in-vacuo and resulting residue purified using flash chromatography (SiO$_2$, 0.5% ethyl acetate in hexanes) to give the title compound as a white solid.

PMR (CDCl$_3$): δ 1.27 (6H, s), 1.29 (6H, s), 1.68 (4H, s), 2.26 (6H, m), 6.45 (1H, s), 6.75 (1H, s), 6.95 (1H, s), 7.07 (1H, s), 7.11 (1H, s), 7.17 (1H, s).

2-[(E)-2-(5,6,7,8-Tetrahydro-3,5,5,8,8-pentamethylnaphthalen-2-yl)propen-1-yl]thiophene-4-carboxylic Acid (Compound 19)

To a solution of 500 mg (1.24 mmol) of 2[-2-(E)-(5,6,7,8-tetrahydro-3,5,5,8,8-pentamethylnaphthalen-2-yl)propen-1-yl]-4-bromothiophene in 15 mL of tetrahydrofuran stirring under argon at −100° C. was added 0.527 g (0.775 mL, 1.24 mmol, 1.6 M in hexanes) of n-BuLi. The reaction was stirred for two minutes and purged with carbon dioxide for 20 minutes. The reaction mixture was then allowed to warm to room temperature, acidified, and extracted using ether.

The ether extracts were washed with water, brine and dried (MgSO$_4$). The solvent was removed in-vacuo and the resulting residue taken-up in aqueous 2N sodium hydroxide and washed with ether. The resulting aqueous layer was acidified using 1N HCl and extracted with ether. The ether layer was washed with water and brine, and dried (MgSO$_4$). The solvent was removed in-vacuo and the resulting material purified by flash chromatography (10% ethyl acetate in hexanes) to give the title compound as a white solid.

PMR (d$^6$-DMSO): δ 1.23 (12H, s), 1.62 (4H, s), 2.21 (3H, s), 2.23 (3H, s), 6.56 (1H, s), 7.07 (1H, s), 7.13 (1H, s), 7.45 (2H, s), 8.24 (2H, s).

(±)-1-(5,6,7,8-Tetrahydro-3,5,5,8,8-pentamethylnaphthalen-2-yl)ethanol

To a solution of 4.17 g (17.1 mmol) of methyl[3,5,5,8,8-pentamethyl(5,6,7,8-tetrahydronaphthalen-2-yl]ketone in methanol at 0° C. was portionwise added 0.77 g (20.4 mmol) of sodium borohydride and the resulting suspension stirred at 0° C. for 4 hours. Solvent was removed in-vacuo and the resulting solid taken-up in water, acidified using 1N HCl, and extracted three times with ether. The ether extracts were washed with water, brine and dried (MgSO$_4$). The solvent was removed in-vacuo and resulting residue purified using flash chromatography (SiO$_2$, 10% ethyl acetate in hexanes) to give a single isomer: the title compound as a white solid.

PMR (CDCl$_3$): δ 1.28 (12H, m), 1.47 (3H, d, J=6.5 Hz), 1.67 (4H, s), 2.49 (3H, s), 5.08 (1H, m), 7.10 (1H, s), 7.45 (1H, s).

[5,6,7,8-Tetrahydro-3,5,5,8,8-pentamethylnaphthalen-2-yl)ethan-1-yl] triphenylphosphonium Bromide (Compound 51)

To a solution of 3.87 g (15.7 mmol) of (±)-1-(5,6,7,8-tetrahydro-3,5,5,8,8-pentamethylnaphthalen-2-yl)ethanol in ether and hexanes at 0° C. under argon, was added 42.4 g (14.9 mL, 157 mmol) of potassium bromide and the resulting mixture stirred for 2 hours. Water was then dropwise added over a period of 30 minutes and the layers separated. The aqueous layer was extracted three times with ether. The ether layers were washed with water, brine, and dried (MgSO$_4$). The solvent was removed in-vacuo and the remaining residue taken-up in benzene. Triphenylphosphine was added and the mixture stirred at room temperature for 24 hours. The mixture was then concentrated in-vacuo and the resulting solid recrystallized from acetonitrile and ethyl acetate and hexanes to give the title compound as a white solid.

PMR (CDCl$_3$): δ 0.61 (3H, s), 0.89 (3H, s), 1.27 (6H, s), 1.62 (4H, m), 1.85 (6H, d), 2.04 (3H, dd), 5.19 (2H, m), 6.62 (1H, d), 7.02 (1H, s), 7.43 (6H, m), 7.68 (6H, m), 7.87 (3H, m).

2-[(E)-(2)-((5,6,7,8-Tetrahydro-3,5,5,8,8-pentamethylnaphthalen-2-yl)propen-1-yl]-5-bromothiophene To a solution of 3.00 g (5.26 mmol) of [(5,6,7,8-tetrahydro-3,5,5,8,8-pentamethylnaphthalen-2-yl)ethan-1-yl]triphenylphosphonium bromide in 60 mL of tetrahydrofuran at −78° C. under argon was dropwise added 2.24 g (3.29 mL, 5.26 mmol, 1.6 M in hexanes) of n-BuLi. The resulting suspension was allowed to warm to room temperature where a solution of 1.01 g (0.63 mL, 5.26 mmol) of 5-bromo-2-thiophenecarboxaldehyde in 10 mL of tetrahydrofuran was dropwise added and the resulting mixture stirred for 20 hours at room temperature and then refluxed for 1 hour. The mixture was acidified using 1N HCL, and extracted three times with ether. The ether extracts were washed with water, brine and dried (MgSO$_4$). The solvent was removed in-vacuo and resulting residue purified using flash chromatography (SiO$_2$, 2% ethyl acetate in hexanes) to give the title compound as a white solid.

PMR (CDCl$_3$): δ 1.28 (12H, s), 1.67 (4H, s), 2.24 (6H, 2×s), 6.45 (1H, s), 6.75 (1H, d, J=3.9 Hz), 6.99 (1H, d, J=3.8 Hz), 7.07 (1H, s), 7.09 (1H, s).

5-[(E)-2-(5,6,7,8-Tetrahydro-3,5,5,8,8-pentamethylnaphthalen-2-yl)propen-1-yl]-2-thiophenecarboxylic Acid (Compound 21)

To a solution of 0.230 g (0.57 mmol) of 2-[(E)-2-((5,6,7,8-tetrahydro-3,5,5,8,8-pentamethylnaphthalen-2-yl)propen-1-yl]-5-bromothiophene in ether was dropwise added 0.67 mL (1.14 mmol, 1.7 M in hexanes) of t-BuLi under argon at −78° C. The resulting mixture was stirred for 1.5 hours, purged with carbon dioxide and allowed to warm to room temperature over a period of 16 hours. The mixture was acidified using 1N HCl and extracted with ether. The ether layer was then washed with water, brine, and dried (MgSO$_4$). Solvent was removed in-vacuo to give a blue solid which was recrystallized using ether in hexanes to give the title compound as a light blue solid.

PMR (d$^6$-DMSO): δ 1.21 (12H, s), 1.60 (4H, s), 2.19 (3H, s), 2.24 (3H, s), 6.45 (1H, s), 6.61 (1H, s), 6.99 (1H, d, J=3.8 Hz), 7.06 (1H, s), 7.12 (1H, s), 7.18 (1H, d, J=3.8 Hz), 7.67 (1H, d, J=3.8 Hz).

Ethyl 5-[(E)-2-(5,6,7,8-Tetrahydro-3,5,5,8,8-pentamethylnaphthalen-2-yl)propen-1-yl]-2-thiophenecarboxylate (Compound 20)

A suspension of 0.161 g (0.437 mmol) of 5-((E)-2-(5,6,7,8-tetrahydro-3,5,5,8,8-pentamethylnaphthalen-2-yl)propen-1-yl)-2-thiophenecarboxylic acid, (Compound 21, 0.03 g, 0.655 mmol) in EtOH, 0.099 g (0.48 mmol) of 1,3-dicyclohexylcarbodiimide, and 5.3 mg (0.044 mmol) of 4-dimethylaminopyridine in 10 mL of methylene chloride was stirred at room temperature for 16 hours. The reaction mixture was filtered and the filtrate washed with water and brine. The organic layers were combined and dried (MgSO$_4$), The solvent was removed in-vacuo and the residue purified using flash chromatography (SiO$_2$, 5% ethyl acetate in hexanes) to give the title compound as a clear oil.

PMR (CDCl$_3$): δ 1.27 (12H, s), 1.39 (3H, t, J=7.2 Hz), 1.68 (4H, s), 2.27 (3H, s), 2.34 (3H, s), 4.37 (2H, q, J=7. Hz), 6.57 (1H, s), 7.00 (1H, d, J=3.8 Hz), 7.09 (1H, s), 7.11 (1H, s), 7.74 (1H, d, J=3.8 Hz).

Ethyl 4-[(E)-2-(2,2,4,4,7-Pentamethyl-chroman-6-yl)propen-1-yl]-benzoate (Compound 24)

A mixture of 2.6 g (8.6 mmol) of ethyl [4-(diethoxyphosphinyl)methyl]benzoate (Compound 40) and 6.0 mL (8.6 mmol) of potassium bis(trimethylsilyl)amide in tetrahydrofuran was stirred for 30 minutes at room temperature under argon. A solution of 1.0 g (4.3 mmol) of methyl (2,2,4,4,7-pentamethylchroman-6-yl) ketone also known as 2,2,4,4,7-pentamethyl-6-acetylchroman (Compound 52) in THF was added and the resulting mixture stirred for 20 hours. To this was added 4.3 mL (8.6 mmol) of 2M sodium ethoxide and the mixture stirred an additional 2 hours. Sodium bicarbonate was then added and the mixture extracted with ether. The ether layer was washed with brine and dried (MgSO$_4$). The solvent was removed in-vacuo and the resulting residue purified using flash chromatography (SiO$_2$, 2% ethyl acetate in hexanes) to give a mixture of isomers which were separated using HPLC (1% ethyl acetate in hexanes) to give the title compound as a clear oil.

PMR (0.1% ethylbenzene in CDCl$_3$): δ 1.37 (6H, s), 1.38 (6H, s), 1.42 (3H, t), 1.84 (4H, s), 2.21 (3H, s), 2.28 (3H, s), 4.41 (2H, q), 6.41 (1H, s), 6.67 (1H, s), 7.10 (1H, s), 7.45 (2H, d, J=8.2 Hz), 8.06 (2H, d, J=8.2 Hz).

4-[(E)-2-(2,2,4,4,7-Pentamethylchroman-6-yl) propen-1-yl]benzoic Acid (Compound 25)

A solution of potassium hydroxide in ethanol was added to ethyl 4-[(E)-2-(2,2,4,4,7-pentamethylchroman-6-yl) propen-1-yl]benzoate (Compound 24) and the resulting mixture stirred at room temperature. Solvent was removed in-vacuo and the resulting solid taken-up in water, acidified using 1N HCl, and extracted three times was ether. The ether extracts were washed with water, brine and dried (MgSO$_4$).

The solvent was removed in-vacuo to give the title compound as a pale yellow solid.

PMR (d⁶-DMSO): δ 1.38 (12H, s), 1.87 (2H, s), 2.23 (3H, s), 2.29 (3H, s), 6.44 (1H, s), 6.68 (1H, s), 7.10 (1H, s), 7.50 (2H, d, J=8.3 Hz), 8.14 (2H, d, J=8.3 Hz).

Ethyl 4-[(E)-2-(2-Methyl-5-tert-butylphenyl)propen-1-yl]benzoate (Compound 26)

A solution of 7.08 g (37 mmol) of 2-methyl-5-t-butylacetophenone (Compound 53) (obtained in accordance with the chemical literature) and 10.42 g (37 mmol) of ethyl [4-(diethoxyphosphinyl)methyl]benzoate (Compound 40) in 30 mL of tetrahydrofuran was added via cannula into a suspension of 1.5 g (37 mmol) of sodium hydride in 30 mL of tetrahydrofuran at 0° C. under argon. The resulting suspension was allowed to warm to room temperature and stirred for 72 hours. The resulting sludge was taken-up in water and 1N HCl and extracted with ether. The ether layers were washed with water, brine, and dried (MgSO₄). The solvent was removed in-vacuo and the residue purified using flash chromatography (SiO₂, 1% ethyl acetate in hexanes) to give a mixture of isomers which were separated using HPLC (0.5% ethyl acetate in hexanes) to give the title compound as a white solid.

PMR (CDCl₃): δ 1.34 (9H, s), 1.41 (3H, t,) 1.69 (4H, s), 2.20 (3H, s), 2.36 (3H, s), 4.38 (2H, q), 6.41 (1H, s), 7.04 (1H, m), 7.12 (1H, m), 7.22 (1H, m), 7.42 (2H, d, J=8.3 Hz), 8.03 (2H, d, J=8.3 Hz).

4-[(E)-2-(2-Methyl-5-tert-butylphenyl)propen-1-yl]benzoic Acid (Compound 27)

A solution of potassium hydroxide in ethanol was added to 41 mg (0.12 mmol) of ethyl 4-[(E)-2-2-methyl-5-tert-butylphenyl)propen-1-yl]benzoate (Compound 26) and the resulting mixture stirred at room temperature. Solvent was removed in-vacuo and the resulting solid taken-up in water, acidified using 1N HCl, and extracted with ether. The ether extracts were washed with water, brine and dried (MgSO₄). The solvent was removed in-vacuo to give the title compound as a yellow solid.

PMR (d⁶-DMSO): δ 1.24 (12H, s), 2.13 (3H, s), 2.28 (3H, s), 6.37 (1H, s), 7.09 (1H, d, J=8.0 Hz), 7.2 (2H, m), 7.49 (2H, d, J=8.3 Hz), 7.95 (2H, d, J=8.3 Hz).

Methyl [3-Chloro-5,5,8,8-tetramethyl(5,6,7,8-tetrahydronaphthalen)-2-yl]ketone (Compound 54)

To a suspension of 13.6 g (102 mmol) of aluminum chloride in 24 mL of methylene chloride at 0° C. under argon was added a solution of 7.98 g (7.23 mL, 102 mmol) of acetyl chloride, 18.88 g (84.8 mmol) of 3-chloro-5,6,7,8-tetrahydro-3,5,5,8,8-pentamethylnaphthalen in 56 mL of methylene chloride. The resulting mixture was allowed to warm to room temperature over a period of three hours with stirring. The mixture was recooled to 0° C. and 1N HCl was added dropwise. The mixture was then taken-up in water and extracted three times with methylene chloride. The organic layers were washed with 1N HCl, water, brine, and dried (MgSO₄). Solvent was removed in-vacuo and the resulting residue purified using distillation (116° C., 3 mm Hg) to give a mixture of starting material and product.

PMR (CDCl₃): δ 1.27 (12H, s), 1.19 (4H, s), 2.65 (3H, s), 7.31 (1H, s), 7.54 (1H, s).

(±)-1-(3-Chloro-5,6,7,8-tetrahydro-5,5,8,8-tetramethylnaphthalen-2-yl)ethanol To a solution of 5.01 g (18.9 mmol) of methyl [3-chloro-5,5,8,8-tetramethyl(5,6,7,8-tetrahydronaphthalen)-2-yl] ketone (Compound 54) in methanol at 0° C. was portionwise added 1.0 g (26.4 mmol) of sodium borohydride and the resulting suspension stirred at 0° C. for 2 hours. The mixture was then acidified using 1N HCl, and extracted three times with ether. The ether extracts were washed with water, brine and dried (MgSO₄). The solvent was removed in-vacuo and resulting residue purified using flash chromatography (SiO₂, 5% ethyl acetate in hexanes) to give the title compound as a white solid.

PMR (CDCl₃): δ 1.26 (12H, m), 1.48 (3H, d, J=6.5 Hz), 1.67 (4H, s), 1.98 (1H, s), 5.21 (1H, m), 7.23 (1H, s), 7.50 (1H, s).

[(3-Chloro-5,6,7,8-tetrahydro-5,5,8,8-tetramethylnaphthalen-2-yl)ethan-1-yl]triphenylphosphonium Bromide (Compound 55)

To a solution of 3.15 g (11.8 mmol) of (±)-1-(3-chloro-5,6,7,8-tetrahydro-5,5,8,8-tetramethylnaphthalen-2-yl) ethanol in ether and hexane stirring at 0° C. under argon, was added dropwise 31.9 g (11.2 mL, 118 mmol) of phosphorus tribromide and the mixture stirred 1.5 hours. Water was then carefully added and the mixture extracted with several portions of ether. The ether extracts were washed with water, sodium bicarbonate, brine, and dried (MgSO₄). The solvent was removed in-vacuo and the residual oil taken up in 175 mL of benzene. To this was added 3.09 g (11.8 mmol) of triphenylphosphine and the solution stirred for 24 hours at room temperature. Purification was done using flash chromatography (SiO₂, 0.5% ethyl acetate in hexanes, 5% MeOH in methylene chloride) to give the title compound as a white foam.

PMR (CDCl₃): δ 0.70 (3H, s), 1.02 (3H, s), 1.28 (12H, d, J=15 Hz), 1.62 (4H, m), 2.01 (3H, dd, J=15, 9 Hz), 5.19 (1H, m), 6.79 (1H, s), 7.4–7.9 (16H, m).

Ethyl 4-[(E)-2-(3-Chloro-5,6,7,8-tetrahydro-5,5,8,8-tetramethylnaphthalen)-2-yl)propen-1-yl]benzoate (Compound 12)

A suspension of 0.91 g (1.54 mmol) of [(3-chloro-5,6,7,8-tetrahydro-5,5,8,8-tetramethylnaphthalen-2-yl)ethan-1-yl]triphenylphosphonium bromide (Compound 55), 0.27 g 1.54 mmol) of freshly distilled 4-carbethoxybenzaldehyde and 5.9 g (7.0 mL, 76.9 mmol) of 1,2-epoxybutane were combined under argon and refluxed for 96 hours. The resulting dark brown solution was concentrated in-vacuo and the residue purified using column chromatography (SiO₂, 2% ethyl acetate in hexanes) to give a mixture of isomers. Separation of isomers was achieved using HPLC (10% water in acetonitrile) to give the title compound as a white solid.

PMR (CDCl₃): δ 1.29 (12H, s), 1.41 (3H, t, J=7.3 Hz), 1.69 (4H, s), 2.24 (3H, s), 2.23 (3H, s), 4.49 (2H, q, J=6.8 Hz), 6.49 (1H, s), 7.20 (1H, s), 7.30 (1H, s), 7.48 (2H, d, J=8.4 Hz), 8.05 (2H, d, J=8.4 Hz).

4[(E)-2-(3-Chloro-5,6,7,8-tetrahydro-5,5,8,8-tetramethylnaphthalen-2-yl)propen-1-yl]benzoic Acid (Compound 13)

A solution of potassium hydroxide in ethanol was added to 20 mg (0.049 mmol) of ethyl 4-[(E)-2-(3-chloro-5,6,7,8-tetrahydro-5,5,8,8-tetramethylnaphthalen-2-yl)propen-1-yl] benzoate (Compound 12) and the resulting mixture stirred at room temperature for 24 hours. Solvent was removed in-vacuo and the resulting solid taken-up in water, acidified using 1N HCl, and extracted three times with ether. The ether extracts were washed with water, brine and dried (MgSO$_4$). The solvent was removed in-vacuo and recrystallized using acetonitrile to give the title compound as a white solid.

PMR (CDCl$_3$): δ 1.29 (12H, s), 1.70 (4H, s), 2.28 (3H, d, J=1.4 Hz), 6.51 (1H, s), 7.20 (1H, s), 7.30 (1H, s), 7.51 (1H, d, J=8.4 Hz), 8.12 (1H, d, J=8.4 Hz).

Ethyl 4-[(E)-2-(2-Methyl-4-tert-butylphenyl)propen-1-yl]benzoate (Compound 28)

A mixture of 3.17 g (10.5 mmol) of ethyl [4-(diethoxyphosphinyl)methyl]benzoate (Compound 40) and 7.6 mL (10.64 mmol) of potassium bis(trimethylsilyl)amide (1.4 M in THF) was stirred for 30 minutes. A solution of 1.0 g (5.3 mmol) of 2-methyl-4-t-butylacetophenone (Compound 56, obtainable in accordance with the chemical literature) in 20 mL of dimethylsulfoxide was added and the solution stirred for 20 hours. Sodium bicarbonate was added and the solution extracted using ether. The ether extracts were washed with water, brine and dried (MgSO$_4$). The solution was concentrated and the residual oil purified using column chromatography (SiO$_2$, 3% ethyl acetate in hexanes) to give a mixture of isomers. Photoisomerization (1 hour, hexane, mercury lamp) increased the yield of trans isomer (45:55, E:Z). Isomers were separated using HPLC (20% water in acetonitrile) to give the title compound as a clear oil.

4-[(E)-2-(2-Methyl-4-tert-butylphenyl)propen-1-yl]benzoic Acid (Compound 29)

A solution of sodium hydroxide, 2-methoxyethanol and ether was added to 70 mg (0.21 mmol) of ethyl 4-[(E)-2-(2-methyl-4-tert-butylphenyl)propen-1-yl]benzoate (Compound 28) and the resulting mixture stirred at room temperature for 5 hours. Solvent was removed in-vacuo and the resulting solid taken-up in water, acidified using 1N HCl, and extracted with ether. The ether extracts were washed with water, brine and dried (MgSO$_4$). The solvent was removed in-vacuo to give the title compound as a yellow solid.

PMR (d$^6$-Acetone): δ 1.30 (9H, s), 2.19 (3H, d, J=1.5 Hz), 2.33 (3H, s), 6.41 (1H, s), 7.12 (1H, d, J=8.0 Hz), 7.23 (2H, m), 7.54 (1H, d, J=8.4 Hz), 8.05 (1H, d, J=8.4 Hz).

3-Bromo-5,6,7,8-tetrahydro-5,5,8,8-tetramethylnaphthalene

To a solution of 25 g (137 mmol) of 1,6-dichloro-1,6-dimethylhexane in 28.9 mL (274 mmol) of bromobenzene was portionwise added 11.0 g (82.2 mmol) of aluminum chloride at 0° C. under argon and the resulting suspension stirred for 5 minutes at 0° C. and allowed to warm to room temperature for 15 minutes. 1N HCl was added dropwise. The mixture was taken-up in water and extracted three times with ether. The ether layers were washed with 1N HCl, sodium bicarbonate, brine, and dried (MgSO$_4$). Purification was done using distillation (110° C., 2 mm Hg) to give the title compound as a yellow solid.

PMR (CDCl$_3$): δ 1.25 (6H, s), 1.27 (6H, s), 1.67 (4H, s), 7.16 (1H, d, J=8.5 Hz), 7.23 (1H, dd, J=2.0, 8.5 Hz), 7.40 (1H, d, J=2.1 Hz).

Methyl [3-Bromo-5,5,8,8-tetramethyl(5,6,7,8-tetrahydronaphthalen)-2-yl]ketone (Compound 57)

To a suspension of 6.16 g (46.3 mmol) of aluminum chloride in methylene chloride at 0° C. under argon was added a solution of 3.29 mL (den=1.104, 46.3 mmol) of acetyl chloride, 10.3 g (38.5 mmol) of 3-bromo-5,5,8-8-tetramethyl-5,6,7,8-tetrahydronaphthalene in methylene chloride. The resulting mixture was stirred for 2 hours and allowed to warm to room temperature over a period of 16 hours. The mixture was recooled to 0° C. and 1N HCl was added dropwise. The mixture was then taken-up in water and extracted three times with methylene chloride. The organic layers were washed with 1N HCl, water, brine, and dried (MgSO$_4$). Solvent was removed in-vacuo and the resulting residue purified using distillation (116° C., 3 mm Hg) to give a mixture of starting material and product.

PMR (CDCl$_3$): δ 1.27 (12H, s), 1.68 (4H, s), 2.64 (3H, s), 7.45 (1H, s), 7.50 (1H, s).

Ethyl 4-[(E)-2-(3-Bromo-5,6,7,8-tetrahydro-5,5,8,8-tetramethylnaphthalen-2-yl)propen-1-yl]benzoate (Compound 14)

A mixture of 5.56 g (18.7 mmol) of ethyl [4-(diethoxyphosphinyl)methyl]benzoate (Compound 40) and 74 mL (18.7 mmol) of potassium bis(trimethylsilyl)amide was stirred for 38 minutes. A solution of 2.0 g (6.5 mmol) of methyl [3-bromo-5,5,8,8-tetramethyl(5,6,7,8-tetrahydronaphthalen)-2-yl]ketone (Compound 57) in 30 mL of dimethylsulfoxide was added and the solution stirred for 64 hours. Sodium bicarbonate was added and the solution extracted using methylene chloride and dried (MgSO$_4$). Solvent was removed in-vacuo and the residual oil purified using flash chromatography (SiO$_2$, 3% ethyl acetate in hexanes).

PMR (CDCl$_3$): δ 1.27 (12H, s), 1.41 (3H, t), 1.68 (4H, s), 2.24 (3H, s), 4.38 (2H, q), 6.45 (1H, s), 7.18 (1H, s), 7.47 (3H, m), 8.04 (1H, s), 8.08 (1H, s).

4[(E)-2-(3-Bromo-5,6,7,8-tetrahydro-5,5,8,8-tetramethylnaphthalen-2-yl)propen-1-yl]benzoic Acid (Compound 15)

A solution of sodium hydroxide, 2-methoxyethanol and ether was added to 50 mg (0.11 mmol) of ethyl 4-[(E)-2-(3-bromo-5,6,7,8-tetrahydro-5,5,8,8-tetramethylnaphthalen-2-yl)propen-1-yl]benzoate (Compound 14) and the resulting mixture stirred at room temperature for 17 hours. Solvent was removed in-vacuo and the resulting solid taken-up in water, acidified using 2N HCl, and extracted with ether. The ether extracts were washed with water, brine and dried (MgSO$_4$). The solvent was removed in-vacuo to give the title compound as a white solid.

PMR (d$^6$-DMSO): δ 1.30 (12H, s), 1.69 (4H, s), 2.26 (3H, d, J=1.3 Hz), 6.48 (1H, s), 7.20 (1H, s), 7.49 (1H, s), 8.14 (2H, d, J=8.3 Hz).

Methyl [3-Ethyl-5,5,8,8-tetramethyl(5,6,7,8-tetrahydronaphthalen)-2-yl]ketone (Compound 58)

To a suspension of 4.59 g (34.4 mmol) of aluminum chloride in 20 mL of methylene chloride at −5° C. under argon was added a solution of 2.32 g (2.10 mL, 29.5 mmol) of acetyl chloride and 4.95 g (23 mmol) of 3-ethyl-5,5,8,8-tetramethyl-5,6,7,8-tetrahydronaphthalene (obtainable in accordance with U.S. Pat. No. 2,897,237, the specification of which is expressly incorporated by reference) in 10 mL of methylene chloride over a period of 1 hour. The resulting mixture was stirred at −10 to +5° C. for 3 hours. The mixture was then taken-up in water and extracted three times with methylene chloride. The organic layers were washed with brine and dried (MgSO$_4$). Solvent was removed in-vacuo and the resulting residue purified using flash chromatography (SiO$_2$, 10% ethyl acetate in hexanes) to give the title compound as a white solid.

PMR (CDCl$_3$): δ 1.20 (3H, t, J=7.5 Hz), 1.29 (6H, s), 1.30 (6H, s), 1.69 (4H, s), 2.57 (3H, s), 2.84 (2H, q, J=7.3 Hz), 7.17 (1H, s), 7.59 (1H, s).

Methyl [3-Isopropyl-5,5,8,8-tetramethyl(5,6,7,8-tetrahydronaphthalen)-2-yl]ketone (Compound 59)

To a suspension of 5.80 g (43.5 mmol) of aluminum chloride in 15 mL of methylene chloride at −5° C. under argon was added a solution of 3.20 g (2.90 mL, 41 mmol) of acetyl chloride and 6.58 g (29 mmol) of 3-isopropyl-5,5,8,8-tetraamethyl-5,6,7,8-tetrahydronaphthalene (obtainable in accordance with U.S. Pat. No. 2,879,237, the specification of which is expressly incorporated by reference) in 25 mL of methylene chloride over a period of 1 hour. The resulting mixture was stirred at −5° C. for 2.5 hours. The mixture was then cooled to 0° C., taken-up in water and extracted three times with hexane. The organic layers were washed with brine and dried (MgSO$_4$). Solvent was removed in-vacuo and the resulting residue purified using flash chromatography (SiO$_2$, 5% ethyl acetate in hexanes) to give the title compound as a white solid.

PMR (CDCl$_3$): δ 1.22 (6H, s), 1.24 (6H, s), 1.29 (6H, s), 1.69 (4H, s), 2.49 (3H, s), 2.56 (3H, s), 3.50 (1H, pentet, J=6.8 Hz), 7.32 (1H, s), 7.46 (1H, s).

Ethyl 5-[(E)-2-(5,6,7,8-Tetrahydro-3,5,5,8,8-pentamethylnaphthalen-2-yl)propen-1-yl]-2-furancarboxylate (Compound 22)

A mixture of sodiumhydride in 10 mL of dimethylsulfoxide was heated at 55° C. for 1 hour and added to 1.159 g (4.00 mmol) of ethyl-2-[5-(diethoxyphosphinyl)methyl]furanoate (Compound 42). The resulting deep red solution was stirred 45 minutes at room temperature and added to a solution of 0.501 g (2.05 mmol) of methyl [3,5,5,8,8-pentamethyl(5,6,7,8-tetrahydronaphthalen)-2-yl]ketone (Compound 50) and the resulting solution stirred at room temperature for 48 hours. Sodium bicarbonate was added and the solution extracted using ether and dried (MgSO$_4$). The solution was concentrated and the residual oil purified using column chromatography (SiO$_2$, 5% ethyl acetate in hexanes). Separation of isomers was achieved using HPLC.

Ethyl 5-[(E)-2-(5,6,7,8-Tetrahydro-3,5,5,8,8-pentamethylnaphthalen-2-yl)propen-1-yl]-3-nicotinoate (Compound 16)

To 0.21 g (0.70 mmol) of ethyl 3-5-(diethoxyphosphinyl)methyl]nicotinoate (Compound 43) stirring at 0° C. under argon was dropwise added 0.90 g (1.0 ml, 1 mmol) of sodium bis(trimethylsilyl)amide (1M in tetrahydrofuran). The resulting deep red solution was stirred 1 hour at room temperature and added to a solution of 0.154 g (0.63 mmol) of methyl [3,5,5,8,8-pentamethyl(5,6,7,8-tetrahydronaphthalen)-2-yl]ketone (Compound 50) and the resulting solution stirred at room temperature for 72 hours. Sodium bicarbonate was added and the solution extracted using ether and dried (MgSO$_4$). The solution was concentrated and ther residual oil purified using column chromatography (SiO$_2$, 5% ethyl acetate in hexanes). Separation of isomers was achieved using HPLC.

What is claimed is:

1. A process for administering to a female mammal, who is in the child bearing age or pregnant, a substantially non-teratogenic pharmaceutical composition containing an effective dose of a compound of the formula

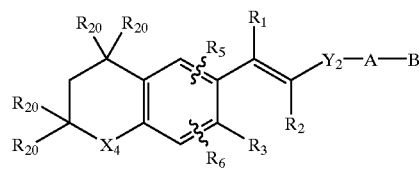

where the symbols are defined as follows:

$X_4$ is O, $Y_2$ is furyl, $R_1$, $R_3$ and $R_{20}$ are methyl, $R_2$, $R_5$ and $R_6$ are hydrogen; A is $(CH_2)_n$ where n is 0; and B is COOH or COOC$_2$H$_5$, said composition being administered to treat or prevent one or more of the diseases and conditions selected from the group consisting of dermatoses, atherosclerosis and restenosis resulting from neointimal hyperproliferation, non-malignant hyperproliferative diseases, chronic inflammatory diseases, diseases associated with lipid metabolism and transport, dry eye syndrome, for promoting wound healing, and for reversing and preventing the effects of sun damage to skin.

2. A process for administering to a female mammal, who is in the child bearing age or pregnant, a substantially non-teratogenic pharmaceutical composition containing an effective dose of a compound of the formula

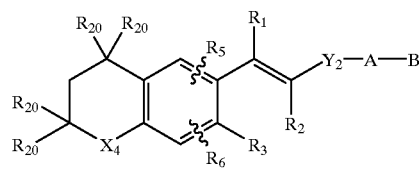

where the symbols are defined as follows:

$X_4$ is S, $Y_2$ is furyl $R_1$ is lower alkyl, Cl, Br, or I;

$R_2$ is H, lower alkyl, Cl, Br, or I;

$R_3$ is lower alkyl, Cl, Br, I, OR$_{11}$, SR$_{11}$, OCOR$_{11}$, SCOR$_{11}$, NH$_2$, NHR$_{11}$, N(R$_{11}$)$_2$, NHCOR$_{11}$, or NR$_{11}$—COR$_{11}$;

$R_5$ and $R_6$ independently are H, lower alkyl, Cl, Br, I, lower alkoxy or lower thioalkoxy of 1 to 6 carbons;

A is $(CH_2)_n$ where n is 0;

B is COOH or a pharmaceutically acceptable salt thereof, or COOR$_8$, R$_8$ is an alkyl group of 1 to 10 carbons, or a cycloalkyl group of 5 to 10 carbons, or R$_8$ is phenyl or lower alkylphenyl;

$R_{20}$ is independently H or lower alkyl;

said composition being administered to treat or prevent one or more of the diseases and conditions selected from the group consisting of dermatoses, atherosclerosis and restenosis resulting from neointimal hyperproliferation, non-malignant hyperproliferative diseases, chronic inflammatory diseases, diseases associated with lipid metabolism and transport, dry eye syndrome, for promoting wound healing, and for reversing and preventing the effects of sun damage to skin and to treat malignant hyperproliferative diseases, autoimmune diseases and immunological disorders.

3. A process for administering to a female mammal, who is in the child bearing age or pregnant, a pharmaceutical composition containing an effective dose of a compound of the formula

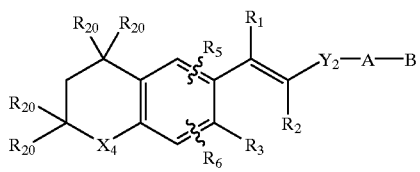

where the symbols are defined as follows:

$R_1$ is lower alkyl, Cl, Br, or I;

$R_2$ is H, lower alkyl, Cl, Br, or I;

$R_3$ is lower alky, Cl, Br, I, $OR_{11}$, $SR_{11}$, $OCOR_{11}$, $SCOR_{11}$, $NH_2$, $NHR_{11}$, $N(R_{11})_2$, $NHCOR_{11}$, or $NR_{11}$—$COR_{11}$;

$R_5$ and $R_6$ independently are H, lower alkyl, Cl, Br, I, lower alkoxy or lower thioalkoxy of 1 to 6 carbons;

A is $(CH_2)_n$ where n is 0–5, lower branched chain-alkyl having 3 to 6 carbons, cycloalkyl having 3 to 6 carbons, alkenyl having 2 to 6 carbons and 1 or 2 double bonds, alkynyl having 2 to 6 carbons and 1 or 2 triple bonds;

B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5 to 10 carbons, or phenyl or lower alkylphenyl, $R_{11}$ is alkyl of 1 to 10 carbons, phenyl or lower alkylphenyl, $R_{12}$ is lower alkyl, and $R_{13}$ is divalent alkyl radical of 2–5 carbons;

$Y_2$ is phenyl, thienyl, furyl pyrrolyl, pyrimidyl, pyrazinyl, pyridazinyl, thiazolyl, imidazolyl and oxazolyl, $R_{20}$ is independently H or lower alkyl;

$X_4$ is S or O, said composition being administered to treat or prevent one or more of the diseases and conditions selected from the group consisting of dermatoses, atherosclerosis and restenosis resulting from neointimal hyperproliferation, non-malignant hyperproliferative diseases, chronic inflammatory diseases, diseases associated with lipid metabolism and transport, dry eye syndrome, for promoting wound healing, and for reversing and preventing the effects of sun damage to skin and to treat malignant hyperproliferative diseases, autoimmune diseases and immunological disorders and wherein the compound has retinoid like biological activity and the following further biological property:

substantial lack of teratogenecity as measured in a test administered for testing teratogenecity in ICR mice, when the compound is administered on the 11th day of gestation of gestating-healthy ICR mice in a single dose of at least 1 mg of compound per kg body weight of the test animal, the compound causes no resorption of fetus and no detectable teratogenic effect in the litter of the test animal.

4. The process of claim 3 where in the test administered to measure teratogenecity, a single dose of at least 10 mg of the compound per kg body weight of the test animal the compound causes no resorption of fetus and no detectable teratogenic effect in the litter of the test animal.

* * * * *

UNITED STATES PATENT AND TRADEMARK OFFICE
CERTIFICATE OF CORRECTION

PATENT NO.     : 6,624,188 B1
DATED          : September 23, 2003
INVENTOR(S)    : Chandratratna et al.

It is certified that error appears in the above-identified patent and that said Letters Patent is hereby corrected as shown below:

Title page,
Item [56], References Cited, U.S. PATENT DOCUMENTS,
"5,053253" should be -- 5,053,523 --
"5,068,523" should be -- 5,068,252 --

Column 5,
Line 64, "the membered ring" should be -- the 5 membered ring --

Column 10,
Line 23, "he present" should be -- the present --
Line 64, "$\leqq$" should be -- $\leq$ --

Column 26,
Line 51, "Feb." should be -- February --

Column 29,
Line 20, "Pentamethyl" should be -- pentamethyl --
Line 29, "O°C."should be -- O°C --

Column 31,
Line 61, "Acid" should be -- acid --

Column 32,
Line 34, "Pentamethylchroman-6-yl" should be -- pentamethylchroman-6-yl --
Line 60, "Acid" should be -- acid --

Column 33,
Line 31, "Acid" should be -- acid --

Column 34,
Line 37, "3-Chloro-5,6,7,8" should be -- 3-chloro-5,6,7,8 --
Line 60, "Acid" should be -- acid --

Column 35,
Line 64, "Bromo" should be -- bromo --

Column 36,
Line 16, "Bromo" should be -- bromo --
Line 38, "Acid" should be -- acid --

UNITED STATES PATENT AND TRADEMARK OFFICE
CERTIFICATE OF CORRECTION

PATENT NO. : 6,624,188 B1
DATED : September 23, 2003
INVENTOR(S) : Chandratratna et al.

It is certified that error appears in the above-identified patent and that said Letters Patent is hereby corrected as shown below:

<u>Column 37,</u>
Line 8, "Isopropyl" should be -- isopropyl --

<u>Column 38,</u>
Line 22, "damage to skin." should be -- damage to skin and to treat malignant hyperproliferative diseases, autoimmune diseases and immunological disorders. --

Signed and Sealed this

Ninth Day of November, 2004

JON W. DUDAS
*Director of the United States Patent and Trademark Office*

UNITED STATES PATENT AND TRADEMARK OFFICE
CERTIFICATE OF CORRECTION

PATENT NO.    : 6,624,188 B1
DATED         : September 23, 2003
INVENTOR(S)   : Chandratrantna et al.

It is certified that error appears in the above-identified patent and that said Letters Patent is hereby corrected as shown below:

Column 38,
Lines 13 and 53, "said composition being" should be deleted.
Lines 17-18 and 57-58, "non-malignant hyperproliferative diseases" should be deleted.

Column 40,
Line 6, "said composition being" should be deleted.
Lines 10-11, "non-malignant hyperproliferative diseases" should be deleted.

Signed and Sealed this

Twenty-second Day of February, 2005

JON W. DUDAS
*Director of the United States Patent and Trademark Office*